US008741308B2

(12) United States Patent
Howley et al.

(10) Patent No.: US 8,741,308 B2
(45) Date of Patent: *Jun. 3, 2014

(54) INTERGENIC REGIONS AS INSERTION SITES IN THE GENOME OF MODIFIED VACCINIA VIRUS ANKARA (MVA)

(71) Applicant: Bavarian Nordic A/S, Kvistgaard (DK)

(72) Inventors: Paul Howley, Berwick (AU); Sonja Leyrer, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/886,093

(22) Filed: May 2, 2013

(65) Prior Publication Data

US 2013/0243813 A1 Sep. 19, 2013

Related U.S. Application Data

(60) Continuation of application No. 13/234,230, filed on Sep. 16, 2011, now Pat. No. 8,435,543, which is a continuation of application No. 12/468,127, filed on May 19, 2009, now Pat. No. 8,034,354, which is a division of application No. 10/514,761, filed as application No. PCT/EP03/05045 on May 14, 2003, now Pat. No. 7,550,147.

(30) Foreign Application Priority Data

May 16, 2002 (DK) ................................ 2002 00752

(51) Int. Cl.

| | |
|---|---|
| *A61K 39/12* | (2006.01) |
| *A61K 39/21* | (2006.01) |
| *A61K 39/193* | (2006.01) |
| *A61K 39/285* | (2006.01) |

(52) U.S. Cl.

USPC .................. 424/199.1; 424/208.1; 424/218.1; 424/232.1

(58) Field of Classification Search

CPC .................... A61K 39/245; A61K 2039/5256; C12N 15/86; C12N 2710/24143; C12N 2830/60; C12N 2710/24122; C12N 2840/20; C12N 2770/24122

See application file for complete search history.

(56) References Cited

U.S. PATENT DOCUMENTS

| | | | |
|---|---|---|---|
| 5,670,367 | A | 9/1997 | Dorner et al. |
| 6,682,742 | B1 | 1/2004 | Wintersperger et al. |
| 7,501,127 | B2 | 3/2009 | Howley et al. |
| 7,550,147 | B2 | 6/2009 | Howley et al. |
| 7,964,374 | B2 | 6/2011 | Howley et al. |
| 8,021,669 | B2 | 9/2011 | Howley et al. |
| 8,029,800 | B2 | 10/2011 | Howley et al. |
| 8,034,354 | B2 | 10/2011 | Howley et al. |
| 8,197,822 | B2 | 6/2012 | Howley et al. |
| 8,198,088 | B2 | 6/2012 | Howley et al. |
| 8,288,125 | B2 | 10/2012 | Howley et al. |
| 8,309,098 | B2 | 11/2012 | Howley et al. |
| 8,309,326 | B2 | 11/2012 | Howley et al. |
| 8,323,661 | B2 | 12/2012 | Howley et al. |
| 8,414,900 | B2 | 4/2013 | Howley et al. |
| 8,435,543 | B2 | 5/2013 | Howley et al. |

FOREIGN PATENT DOCUMENTS

| | | | |
|---|---|---|---|
| EP | 0753581 | A1 | 1/1997 |
| EP | 1146125 | A1 | 10/2001 |
| WO | 9702355 | A1 | 1/1997 |
| WO | 98/13500 | A1 | 4/1998 |

OTHER PUBLICATIONS

Antoine et al. The Complete Genomic Sequence of the Modified Vaccinia Ankara Strain: Comparison with Other Orthopoxviruses. Virology 244(2),1998.

Spehner et al. Construction of fowlpox virus vectors with intergenic insertions: expression of the beta-galactosidase gene and the measles virus fusion gene. Journal of Virology, Feb. 1990, vol. 64, No. 2, p. 527-533.

Men et al. Immunization of rhesus monkeys with a recombinant of modified vaccinia virus Ankara expressing a truncated envelope glycoprotein of dengue type 2 virus indiced resistance to dengue type 2 virus challenge. Vaccine 18:3113-3122, 2000.

Ondondo et al. Immunisation with recombinant modified vaccinia virus Ankara expressing HIV-1 gag in HIV-1-infected subjects stimulates broad functional CD4+ T cell responses. European Journal of Immunology 2006, vol. 36, p. 2585-2594.

Hu, Non-Human Primate Models for AIDS Vaccine Research. Current Drug Targets—Infectious Disorders, Jun. 2005, vol. 5, No. 2, p. 193-201.

Derosiers. Prospects for an AIDS vaccine. Nature Medicine Mar. 2004, vol. 10, No. 3, p. 221-223.

Leslie et al. HIV evolution: CTL escape mutation and reversion after transmission. Nature Medicine Mar. 2004 vol. 10, No. 3, pp. 282-289.

Altman et al. HIV escape: there and back again. Nature Medicine Mar. 2004 vol. 10, No. 3, p. 229-230.

Friedrich et al. Reversion of CTL escape—variant immunodeficiency viruses in vivo. Nature Medicine Mar. 2004 vol. 10, No. 3, p. 275-281.

Tonini et al. Current approaches to developing a preventative HIV vaccine. Current Opinion in Investigational Drugs 2005, vol. 6, No. 2, p. 155-162. Abstract only.

Meyer et al. Mapping of deletions in the genome of the highly . . . Journal of General Virology (1991), 72, 1031-1038.

Scheiflinger et al. Evaluation of the thymidine kinase (tk) locus as an insertion site in . . . Arch Virol (1996)141: 663-669.

Smith et al., Host range selection of vaccinia recombinants containing insertions of foreign genes into non-coding sequences, Vaccine 11 (1):43-53 (1993).

*Primary Examiner* — Louise Humphrey

(74) *Attorney, Agent, or Firm* — Law Office of Salvatore Arrigo and Scott Lee, LLP

(57) ABSTRACT

The present invention relates to novel insertion sites useful for the integration of exogenous sequences into the Modified Vaccinia Ankara (MVA) virus genome. The present invention further provides plasmid vectors to insert exogenous DNA into the genome of MVA. Furthermore, the present invention provides recombinant MVA comprising an exogenous DNA sequence inserted into the new insertion site as medicine or vaccine.

20 Claims, 28 Drawing Sheets

INTERGENIC REGIONS AS INSERTION SITES IN THE GENOME OF MODIFIED VACCINIA VIRUS ANKARA (MVA)

CROSS-REFERENCE TO RELATED APPLICATIONS

This application is a continuation of U.S. application Ser. No. 13/234,230 (now U.S. Pat. No. 8,435,543), filed on Sep. 16, 2011, continuation of U.S. application Ser. No. 12/468,127 (now U.S. Pat. No. 8,034,354), filed on May 19, 2009, which is a continuation of U.S. application Ser. No. 10/514,761 (now U.S. Pat. No. 7,550,147), filed on Nov. 16, 2004, which was the National Stage of International Application PCT/EP03/05045, filed May 14, 2003, which claims the benefit of PA 2002 00752, filed on May 16, 2002, in Denmark and PA 2002 00753, filed on May 16, 2002, in Denmark, all of which are incorporated herein by reference.

The present invention relates to novel insertion sites useful for the integration of exogenous DNA sequences into the MVA genome.

BACKGROUND OF THE INVENTION

Modified Vaccinia Virus Ankara (MVA) is a member of the Orthopoxvirus family and has been generated by about 570 serial passages on chicken embryo fibroblasts of the Ankara strain of Vaccinia virus (CVA) (for review see Mayr, A., et al. [1975], Infection 3, 6-14). As a consequence of these passages the resulting MVA virus contains 31 kilobases less genomic information compared to CVA and is highly host cell restricted (Meyer, H. et al., J. Gen. Virol. 72, 1031-1038 [1991]). MVA is characterized by its extreme attenuation, namely by a diminished virulence or infectiosity but still an excellent immunogenicity. When tested in a variety of animal models, MVA was proven to be avirulent even in immunosuppressed individuals. More importantly, the excellent properties of the MVA strain have been demonstrated in extensive clinical trials (Mayr et al., Zbl. Bakt. Hyg. I, Abt. Org. B 167, 375-390 [1987]). During these studies in over 120,000 humans, including high risk patients, no side effects were seen (Stickl et al., Dtsch. med. Wschr. 99, 2386-2392 [1974]).

It has been further found that MVA is blocked in the late stage of the virus replication cycle in mammalian cells (Sutter, G. and Moss, B. [1992] Proc. Natl. Acad. Sci. USA 89, 10847-10851). Accordingly, MVA fully replicates its DNA, synthesizes early, intermediate and late gene products, but is not capable to assemble mature infectious virions, which could be released from an infected cell. For this reason, namely to be replication restricted, MVA was proposed to serve as a gene expression vector.

More recently, MVA was used to generate recombinant vaccines, expressing antigenic sequences inserted either at the site of the tymidine-kinase (tk) gene (U.S. Pat. No. 5,185,146) or at the site of a naturally occurring deletion within the MVA genome (PCT/EP96/02926).

Although the tk insertion locus is widely used for the generation of recombinant poxviruses, particularly for the generation of recombinant Vaccinia viruses (Mackett, et al. [1982] P.N.A.S. USA 79, 7415-7419) this technology was not applicable for MVA. It was shown by Scheiflinger et al., that MVA is much more sensitive to modifications of the genome compared to other poxviruses, which can be used for the generation of recombinant poxviruses. Scheiflinger et al. showed in particular that one of the most commonly used site for the integration of heterologous DNA into poxviral genomes, namely the thymidine kinase (tk) gene locus, cannot be used to generate recombinant MVA. Any resulting tk(−) recombinant MVA proved to be highly unstable and upon purification immediately deleted the inserted DNA together with parts of the genomic DNA of MVA (Scheiflinger et al. [1996], Arch Virol 141: pp 663-669).

Instability and, thus, high probability of genomic recombination is a known problem within pox virology. Actually, MVA was established during long-term passages exploiting the fact that the viral genome of CVA is unstable when propagated in vitro in tissue cultured cells. Several thousands of nucleotides (31 kb) had been deleted from the MVA genome, which therefore is characterized by 6 major and numerous small deletions in comparison to the original CVA genome.

The genomic organization of the MVA genome has been described recently (Antoine et al. [1998], Virology 244, 365-396). The 178 kb genome of MVA is densely packed and comprises 193 individual open reading frames (ORFs), which code for proteins of at least 63 amino acids in length. In comparison with the highly infectious Variola virus and also the prototype of Vaccinia virus, namely the strain Copenhagen, the majority of ORFs of MVA are fragmented or truncated (Antoine et al. [1998], Virology 244, 365-396). However, with very few exceptions all ORFs, including the fragmented and truncated ORFs, get transcribed and translated into proteins. In the following, the nomenclature of Antoine et al. is used and—where appropriate—the nomenclature based on Hind III restriction enzyme digest is also indicated.

So far, only the insertion of exogenous DNA into the naturally occurring deletion sites of the MVA genome led to stable recombinant MVAs (PCT/EP96/02926). Unfortunately, there is only a restricted number of naturally occurring deletion sites in the MVA genome. Additionally it was shown that other insertion sites, such as, e.g., the tk gene locus, are hardly useful for the generation of recombinant MVA (Scheiflinger et al. [1996], Arch Virol 141: pp 663-669).

OBJECT OF THE INVENTION

It is an object of the present invention to identify further insertion sites of the MVA genome and to provide insertion vectors, which direct the insertion of exogenous DNA sequences into said newly identified insertion sites of the MVA genome.

It is a further object of the present invention to provide a recombinant MVA, which comprises exogenous DNA sequences stably integrated into new insertion sites of the MVA genome.

DETAILED DESCRIPTION OF THE INVENTION

Figure 1A:
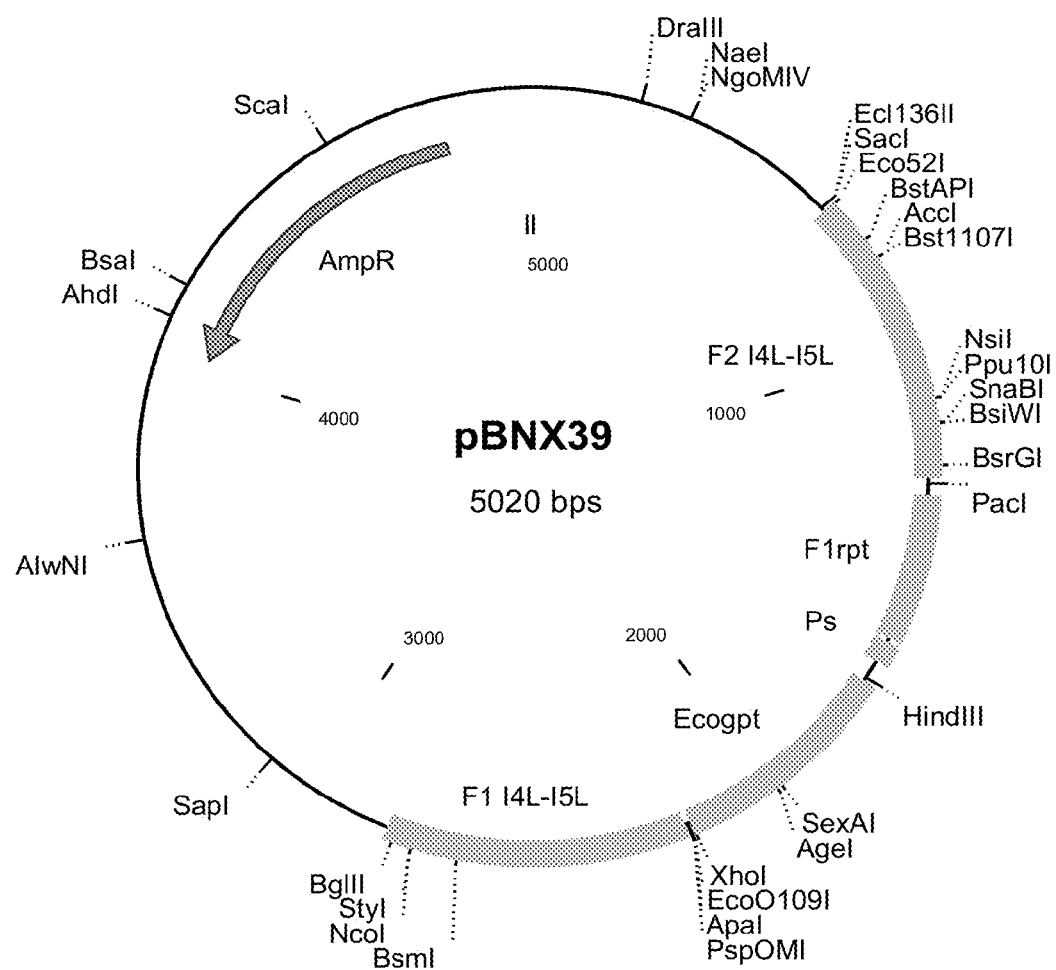

The inventors of the present invention identified new sites for the insertion of exogenous DNA sequences into the genome of Modified Vaccinia Ankara (MVA) virus. The new insertion sites are located in the intergenic regions (IGRs) of the viral genome, wherein said IGRs are, in turn, located between or are flanked by two adjacent open reading frames (ORFs) of the MVA genome.

Accordingly, the present invention relates to a recombinant MVA comprising a heterologous DNA sequence inserted into an IGR of the viral genome. According to the present invention, one or more exogenous DNA sequences may be inserted into one or more IGRs.

It was surprisingly found that exogenous DNA sequences remain indeed stable inserted into IGRs of the MVA genome: As already indicated above, the genome of MVA is to be considered as being quite unstable. It seems that genes or DNA sequences non-essential for propagation of the virus are deleted or fragmented. Although it was—also surprisingly—found that stable recombinant MVAs are obtained when heterologous DNA sequences are inserted into the naturally occurring deletion sites of the MVA genome (PCT/EP96/02926) it was—on the other hand—found that host range genes as, e.g., the tk-locus widely used for the generation of other recombinant poxviruses are no suitable insertion sites in MVA. The fact that Vero-MVA has one extra genomic deletion (PCT/EP01/02703) also suggests that the genome is dynamic in the sense it readily deletes genes that are not required for propagation. Therefore, it could be concluded that inserting heterologous DNA sequences non-essential for viral propagation into spaces between ORFs would be expected to be deleted by the virus as well.

While the nucleotide sequence of an ORF encodes an amino acid sequence forming a peptide, polypeptide or protein, the IGRs between two ORFs have no coding capacity, but may comprise regulatory elements, binding sites, promoter and/or enhancer sequences essential for or involved in the transcriptional control of the viral gene expression. Thus, the IGR may be involved in the regulatory control of the viral life cycle. However, the inventors of the present invention have also shown that the new insertion sites have the unexpected advantage that exogenous DNA sequences can be stably inserted into the MVA genome without influencing or changing the typical characteristics and gene expression of MVA. The new insertion sites are especially useful, since no ORF or coding sequence of MVA is altered.

Moreover, it was surprisingly found that the expression level of a foreign gene inserted into an IGR is higher than the expression level of a foreign gene inserted into a deletion site of the MVA genome (see also Example 1).

The nucleotide sequence of an ORF regularly starts with a start codon and ends with a stop codon. Depending on the orientation of the two adjacent ORFs the IGR, the region in between these ORFs, is flanked either by the two stop codons of the two adjacent ORFs, or, by the two start codons of the two adjacent ORFs, or, by the stop codon of the first ORF and the start codon of the second ORF, or, by the start codon of the first ORF and the stop codon of the second ORF.

Accordingly, the insertion site for the exogenous DNA sequence into the IGR may be downstream or 3' of the stop codon of a first ORF. In case the adjacent ORF, also termed second ORF, has the same orientation as the first ORF, this insertion site downstream of the stop codon of the first ORF lies upstream or 5' of the start codon of the second ORF.

In case the second ORF has an opposite orientation relative to the first ORF, which means the orientation of the two adjacent ORFs points to each other, then the insertion site lies downstream of the stop codons of both ORFs.

As a third alternative, in case the two adjacent ORFS read in opposite direction, but the orientation of the two adjacent ORFs points away from each other, which is synonymous with a positioning that is characterized in that the start codons of the two ORFs are adjacent to each other, then the exogenous DNA is inserted upstream relative to both start codons.

ORFs in the MVA genome occur in two coding directions. Consequently, the Polymerase activity occurs from left to right, i.e., forward direction and, correspondingly, from right to left (reverse direction). It is common practice in poxvirology and it became a standard classification for Vaccinia viruses to identify ORFs by their orientation and their position on the different HindIII restriction digest fragments of the genome. For the nomenclature, the different HindIII fragments are named by descending capital letters corresponding with their descending size. The ORF are numbered from left to right on each HindIII fragment and the orientation of the ORF is indicated by a capital L (standing for transcription from right to Left) or R (standing for transcription from left to Right). Additionally, there is a more recent publication of the MVA genome structure, which uses a different nomenclature, simply numbering the ORF from the left to the right end of the genome and indicating their orientation with a capital L or R (Antoine et al. [1998], Virology 244, 365-396). As an example the I4L ORF, according to the old nomenclature, corresponds to the 064L ORF according to Antoine et al. If not indicated differently, the present invention uses the nomenclature according to Antoine et al.

According to the present invention, heterologous DNA sequences can be inserted into one or more IGRs inbetween two adjacent ORFs selected from the group comprising:

001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052R-053R, 053R-054R, 054R-055R, 055R-056L, 061L-062L, 064L-065L, 065L-066L, 066L-067L, 077L-078R, 078R-079R, 080R-081R, 081R-082L, 082L-083R, 085R-086R, 086R-087R, 088R-089L, 089L-090R, 092R-093L, 094L-095R, 096R-097R, 097R-098R, 101R-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133R-134R, 134R-135R, 136L-137L, 137L-138L, 141L-142R, 143L-144R, 144R-145R, 145R-146R, 146R-147R, 147R-148R, 148R-149L, 152R-153L, 153L-154R, 154R-155R, 156R-157L, 157R-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185L-186R, 186R-187R, 187R-188R, 188R-189R, 189R-190R, 192R-193R.

According to the old nomenclature, ORF 006L corresponds to C10L, 019L corresponds to C6L, 020L to N1L, 021L to N2L, 023L to K2L, 028R to K7R, 029L to F1L, 037L to F8L, 045L to F15L, 050L to E3L, 052R to E5R, 054R to E7R, 055R to E8R, 056L to E9L, 062L to I1L, 064L to I4L, 065L to I5L, 081R to L2R, 082L to L3L, 086R to J2R, 088R to J4R, 089L to J5L, 092R to H2R, 095R to H5R, 107R to D10R, 108L to D11L, 122R to A11R, 123L to A12L, 125L to AI4L, 126L to AI5L, 135R to A24R, 136L to A25L, 137L to A26L, 141L to A30L, 148R to A37R, 149L to A38L, 152R to A40R, 153L to A41L, 154R to A42R, 157L to A44L, 159R to A46R, 160L to A47L, 165R to A56R, 166R to A57R, 167R to B1R, 170R to B3R, 176R to B8R, 180R to B12R, 184R to B16R, 185L to B17L, and 187R to B19R.

Preferably, the heterologous sequence is inserted into an IGR flanked by two adjacent ORFS selected from the group comprising 007R-008L, 018L-019L, 044L-045L, 064L-065L, 136L-137L, 148R-149L.

Heterologous or exogenous DNA sequences are sequences which, in nature, are not normally found associated with the poxvirus as used according to the present invention. According to a further embodiment of the present invention, the exogenous DNA sequence comprises at least one coding sequence. The coding sequence is operatively linked to a transcription control element, preferably to a poxviral transcription control element. Additionally, also combinations between poxviral transcription control element and, e.g., internal ribosomal entry sites can be used.

According to a further embodiment, the exogenous DNA sequence can also comprise two or more coding sequences linked to one or several transcription control elements. Preferably, the coding sequence encodes one or more proteins, polypeptides, peptides, foreign antigens or antigenic epitopes, especially those of therapeutically interesting genes.

Therapeutically interesting genes according to the present invention may be genes derived from or homologous to genes of pathogenous or infectious microorganisms which are disease causing. Accordingly, in the context of the present invention such therapeutically interesting genes are presented to the immune system of an organism in order to affect, preferably induce a specific immune response and, thereby, vaccinate or prophylactically protect the organism against an infection with the microorganism. In further preferred embodiments of the present invention the therapeutically interesting genes are selected from genes of infectious viruses, e.g.,—but not limited to—Dengue virus, Japanese encephalitis virus, Hepatitis virus B or C, or immunodeficiency viruses such as HIV.

Genes derived from Dengue virus are preferably NS1 and PrM genes, wherein said genes may be derived from one, two, three or from all of the 4 Dengue virus serotypes. The NS1 gene is preferably derived from Dengue virus serotype 2 and is preferably inserted into the IGR between the ORFs 064L-065L (I4L-I5L). PrM genes, preferably derived from all of the 4 Dengue virus serotypes, are preferably inserted into the IGRs between the ORFs selected from 007R-008L, 044L-045L, 136L-137L, 148R-149L. More preferably, the PrM gene derived from Dengue virus serotype 1 (prM 1) is inserted into the IGR of 148R-149L, PrM 2 into the IGR 007R-008L, PrM 3 into the IGR of the ORFs 044L-045L, and PrM 4 into the IGR 136L-137L.

According to a further preferred embodiment of the present invention the heterologous DNA sequence is derived from HIV and encodes HIV env, wherein the HIV env gene is preferably inserted into the IGR between the ORFs 007R-008L.

Furthermore, therapeutically interesting genes according to the present invention also comprise disease related genes, which have a therapeutic effect on proliferative disorder, cancer or metabolic diseases. For example, a therapeutically interesting gene regarding cancer could be a cancer antigen that has the capacity to induce a specific anti-cancer immune reaction.

According to a further embodiment of the present invention, the coding sequence comprises at least one marker or selection gene.

Selection genes transduce a particular resistance to a cell, whereby a certain selection method becomes possible. The skilled practitioner is familiar with a variety of selection genes, which can be used in a poxviral system. Among these are, e.g., Neomycin resistance gene (NPT) or Phosphoribosyl transferase gene (gpt).

Marker genes induce a colour reaction in transduced cells, which can be used to identify transduced cells. The skilled practitioner is familiar with a variety of marker genes, which can be used in a poxviral system. Among these are the gene encoding, e.g., β-Galactosidase (β-gal), β-Glucosidase (β-glu), Green Fluorescence protein (EGFP) or Blue Fluorescence Protein.

According to still a further embodiment of the present invention the exogenous DNA sequence comprises a spacing sequence, which separates poxviral transcription control element and/or coding sequence in the exogenous DNA sequence from the stop codon and/or the start codon of the adjacent ORFs. This spacer sequence between the stop/start codon of the adjacent ORF and the inserted coding sequence in the exogenous DNA has the advantage to stabilize the inserted exogenous DNA and, thus, any resulting recombinant virus. The size of the spacer sequence is variable as long as the sequence is without own coding or regulatory function.

According to a further embodiment, the spacer sequence separating the poxviral transcription control element and/or the coding sequence in the exogenous DNA sequence from the stop codon of the adjacent ORF is at least one nucleotide long.

According to another embodiment of the present invention, the spacing sequence separating the poxviral transcription control element and/or the coding sequence in the exogenous DNA sequence from the start codon of the adjacent ORF is at least 30 nucleotides. Particularly, in cases where a typical Vaccinia virus promoter element is identified upstream of a start codon the insertion of exogenous DNA may not separate the promoter element from the start codon of the adjacent ORF. A typical Vaccinia promoter element can be identified by scanning for e.g. the sequence "TAAAT" for late promoters (Davison & Moss, J. Mol. Biol. 1989; 210: 771-784) and an A/T rich domain for early promoters. A spacing sequence of about 30 nucleotides is the preferred distance to secure that a poxviral promoter located upstream of the start codon of the ORF is not influenced. Additionally, according to a further preferred embodiment, the distance between the inserted exogenous DNA and the start codon of the adjacent ORF is around 50 nucleotides and more preferably around 100 nucleotides.

According to a further preferred embodiment of the present invention, the spacing sequence comprises an additional poxviral transcription control element which is capable to control the transcription of the adjacent ORF.

A typical MVA strain which can be used according to the present invention for generating a recombinant MVA is MVA-575 that has been deposited at the European Collection of Animal Cell Cultures under the deposition number ECACC V00120707.

Another preferred MVA strain is MVA-Vero or a derivative thereof. MVA-Vero strains have been deposited at the European Collection of Animal Cell Cultures under the deposition numbers ECACC V99101431 and 01021411. The safety of the MVA-Vero is reflected by biological, chemical and physical characteristics as described in the International Patent Application PCT/EP01/02703. In comparison to other MVA strains, the Vero-MVA includes one additional genomic deletion.

Still another, more preferred MVA strain is MVA-BN. MVA-BN has been deposited at the European Collection of Animal Cell Cultures with the deposition number ECACC V00083008. MVA-BN virus is an extremely attenuated virus also derived from Modified Vaccinia Ankara virus (see also PCT/EP01/13628).

The term "derivatives" of a virus according to the present invention refers to progeny viruses showing the same characteristic features as the parent virus but showing differences in one or more parts of its genome. The term "derivative of MVA" describes a virus, which has the same functional characteristics compared to MVA. For example, a derivative of MVA-BN has the characteristic features of MVA-BN. One of these characteristics of MVA-EN or derivatives thereof is its attenuation and lack of replication in human HaCat cells.

The recombinant MVA according to the present invention is useful as a medicament or vaccine. It is, according to a further embodiment, used for the introduction of the exogenous coding sequence into a target cell, said sequence being either homologous or heterologous to the genome of the target cell.

The introduction of an exogenous coding sequence into a target cell may be done in vitro to produce proteins, polypeptides, peptides, antigens or antigenic epitopes. This method comprises the infection of a host cell with the recombinant MVA according to the invention, cultivation of the infected host cell under suitable conditions, and isolation and/or enrichment of the polypeptide, peptide, protein, antigen, epitope and/or virus produced by said host cell.

Furthermore, the method for introduction of one or more homologous or one or more heterologous sequence into cells may be applied for in vitro and in vivo therapy. For in vitro therapy, isolated cells that have been previously (ex vivo) infected with the recombinant MVA according to the invention are administered to the living animal body for affecting, preferably inducing an immune response. For in vivo therapy, the recombinant poxvirus according to the invention is directly administered to the living animal body for affecting, preferably inducing an immune response. In this case, the cells surrounding the site of inoculation, but also cells where the virus is transported to via, e.g., the blood stream, are directly infected in vivo by the recombinant MVA according to the invention. After infection, these cells synthesize the proteins, peptides or antigenic epitopes of the therapeutic genes, which are encoded by the exogenous coding sequences and, subsequently, present them or parts thereof on the cellular surface. Specialized cells of the immune system recognize the presentation of such heterologous proteins, peptides or epitopes and launch a specific immune response.

Since the MVA is highly growth restricted and, thus, highly attenuated, it is useful for the treatment of a wide range of mammals including humans, including immune-compromised animals or humans. The present invention also provides pharmaceutical compositions and vaccines for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant poxvirus according to the invention is converted into a physiologically acceptable form. This can be done based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titre of 5×10E8 TCID$_{50}$/ml formulated in about 10 mM Tris, 140 mM NaCl pH 7.4. For the preparation of vaccine shots, e.g., 10E2-10E8 particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e. parenterally, subcutaneous, intramuscularly, by scarification or any other path of administration know to the skilled practitioner. The mode of administration, the dose and the number of administrations can be optimized by those skilled in the art in a known manner. However, most commonly a patient is vaccinated with a second shot about one month to six weeks after the first vaccination shot.

The present invention further relates to plasmid vectors, which can be used to generate recombinant MVA according, to the present invention, and also relates to certain DNA sequences:

Regularly, the IGR located between or flanked by two adjacent ORFs comprises nucleotide sequences in which the exogenous DNA sequence of interest can be inserted. Accordingly, the plasmid vector according to the present invention comprises a DNA sequence derived from or homologous to the genome of MVA, wherein said DNA sequence comprises a complete or partial fragment of an IGR sequence located between or flanked by two adjacent ORFs of the viral genome. Preferably, the plasmid vector comprises inserted into said IGR-derived sequence at least one cloning site for the insertion of an exogenous DNA sequence of interest and, preferably, for the insertion of a poxviral transcription control element operatively linked to said heterologous DNA sequence. Optionally, the plasmid vector comprises a reporter- and/or selection gene cassette. The plasmid vector preferably also comprises sequences of the two adjacent ORFs flanking said complete or partial fragment of the IGR sequence.

Some IGRs have been identified which do not include nucleotide sequences. In these cases, the plasmid vector comprises DNA sequences of the IGR flanking sequences, i.e., DNA sequences of the two adjacent ORFs. Preferably, the cloning site for the insertion of the heterologous DNA sequence is inserted into the IGR. The DNA of the IGR flanking sequences is used to direct the insertion of exogenous DNA sequences into the corresponding IGR in the MVA genome. Such a plasmid vector may additionally include a complete or partial fragment of an IGR sequence which comprises the cloning site for the insertion of the heterologous DNA sequence and, optionally, of the reporter- and/or selection gene cassette.

IGR-DNA sequences as well as IGR flanking sequences of the two adjacent ORFs are preferably selected from IGRs and ORFs, respectively, selected from the group comprising 001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052R-053R, 053R-054R, 054R-055R, 055L-056L, 061L-062L, 064L-065L, 065L-066L, 066L-067L, 077L-078R, 078R-079R, 080R-081R, 081R-082L, 082L-083R, 085R-086R, 086R-087R, 088R-089L, 089L-090R, 092R-093L, 094L-095R, 096R-097R, 097R-098R, 1018-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133L-134R, 134R-135R, 136L-137L, 137L-138L, 141L-142R, 143L-144R, 144R-145R, 145R-146R, 146R-147R, 147R-148R, 148R-149L, 152R-153L, 153L-154R, 154R-155R, 156R-157L, 157L-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185L-186R, 186R-187R, 187R-188R, 188R-189R, 189R-190R, 192R-193R.

The sequences are, more preferably, selected from IGRs and ORFs, respectively, selected from the group comprising 007R-008L, 018L-019L, 044L-045L, 064L-065L, 136L-137L, 148L-149L. IGR derived sequences are, preferably, selected from the group comprising the nucleotide sequences
- no. 527-608 of SeqID No. 32;
- no. 299-883 of SeqID No. 33;
- no. 339-852 of SeqID No. 34;
- no. 376-647 of SeqID No. 35;
- no. 597-855 of SeqID No. 36;
- no. 400-607 of SeqID No. 37.

IGR flanking sequences of the two adjacent ORFS are, preferably, selected from the group comprising the nucleotide sequences:
- no. 1-525 and 609-1190 of SeqID No. 32;
- no. 101-298 and 884-1198 of SeqID No. 33;
- no. 1-338 and 853-1200 of SeqID No. 34;
- no. 1-375 and 648-1200 of SeqID No. 35;
- no. 1-596 and 856-1200 of SeqID No. 36;
- no. 1-399 and 608-1081 of SeqID No. 37.

The DNA sequences are preferably derived from or homologous to the genome of the MVA deposited at ECACC under deposition number V00083008.

To generate a plasmid vector according to the present invention the sequences are isolated and cloned into a standard cloning vector, such as pBluescript (Stratagene), wherein they flank the exogenous DNA to be inserted into the MVA genome. Optionally, such a plasmid vector comprises a selection- or reporter gene cassette, which can be deleted from the final recombinant virus, due to a repetitive sequence included into said cassette.

Methods to introduce exogenous DNA sequences by a plasmid vector into an MVA genome and methods to obtain recombinant MVA are well known to the person skilled in the art and, additionally, can be deduced from the following references:
- *Molecular Cloning*, A laboratory Manual. Second Edition. By J. Sambrook, E. F. Fritsch and T. Maniatis. Cold Spring Harbor Laboratory Press. 1989: describes techniques and know how for standard molecular biology techniques such cloning of DNA, RNA isolation, western blot analysis, RT-PCR and PCR amplification techniques;
- *Virology Methods Manual*. Edited by Brian W J Mahy and Hillar O Kangro. Academic Press. 1996: describes techniques for the handling and manipulation of viruses;
- *Molecular Virology*: A Practical Approach. Edited by A J Davison and R M Elliott. The Practical Approach Series. IRL Press at Oxford University Press. Oxford 1993. Chapter 9: Expression of genes by Vaccinia virus vectors;
- *Current Protocols in Molecular Biology*. Publisher: John Wiley and Son Inc. 1998. Chapter 16, section IV: Expression of proteins in mammalian cells using Vaccinia viral vector: describes techniques and know-how for the handling, manipulation and genetic engineering of MVA.

The MVA according to the present invention, preferably the MVA deposited at ECACC under deposition number V00083008, may be produced by transfecting a cell with a plasmid vector according to the present invention, infecting the transfected cell with an MVA and, subsequently, identifying, isolating and, optionally, purifying the MVA according to the invention.

The DNA sequences according to the invention can be used to identify or isolate the MVA or its derivatives according to the invention and cells or individuals infected with an MVA according to the present invention. The DNA sequences are, e.g., used to generate PCR-primers, hybridization probes or are used in array technologies.

SHORT DESCRIPTION OF THE FIGURES

Figure 1B:
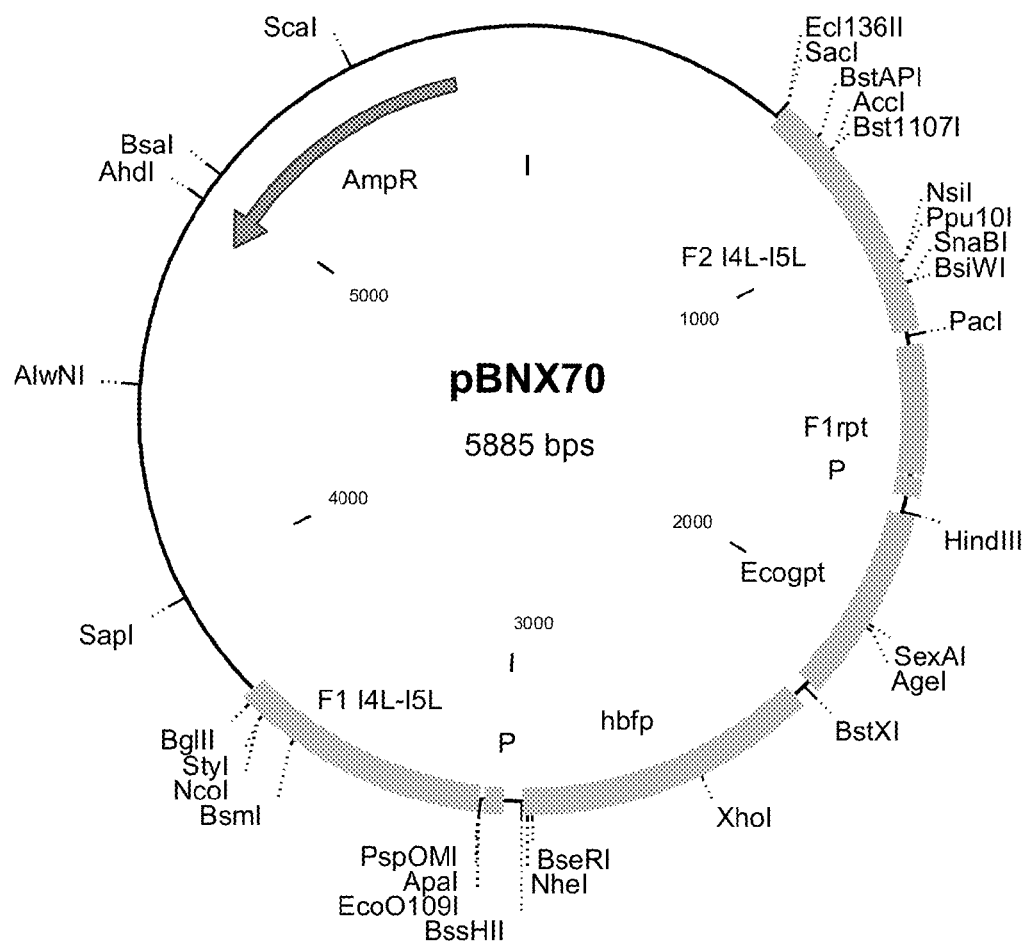
Figure 1C:
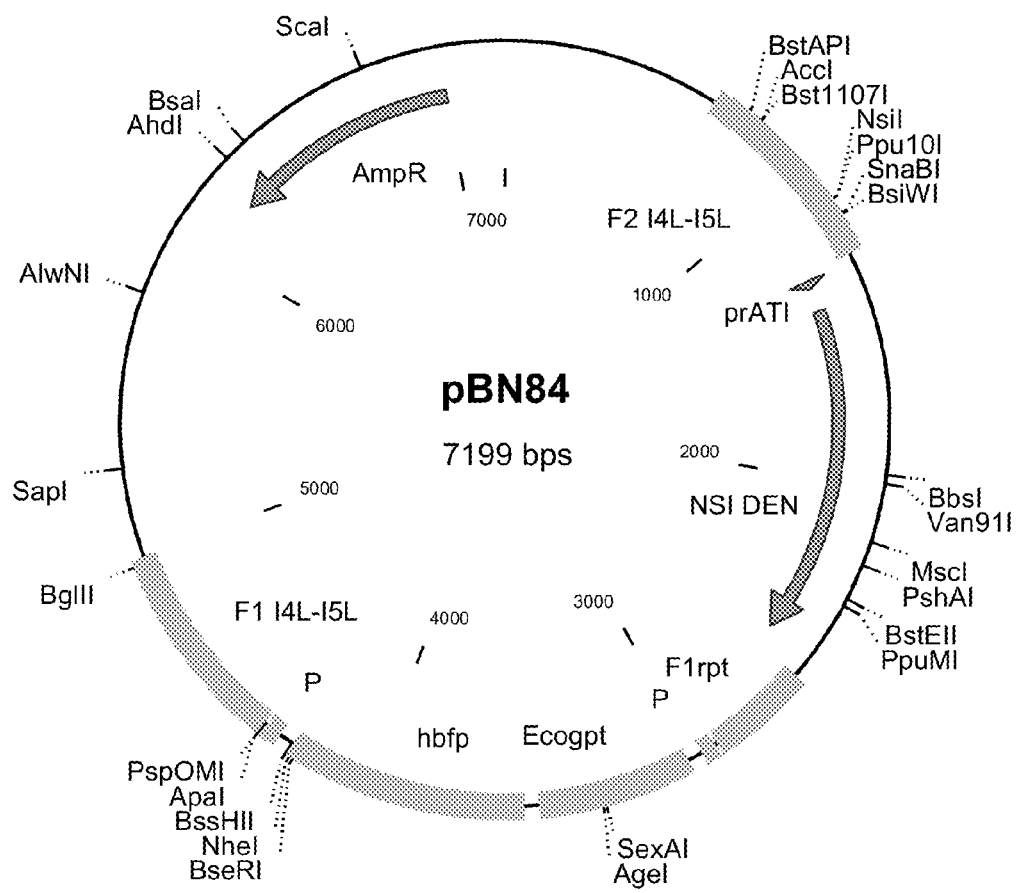

FIG. 1: Restriction map of the vector constructs pBNX39 (FIG. 1a), pBNX70 (FIG. 1b) and pBN84 (FIG. 1c), comprising about 600 bp of MVA sequences flanking the insertion site after the I4L ORF. The plasmids additionally comprise exogenous DNA (Ecogpt and hBFP, respectively) under the transcriptional control of a poxvirus promoter P) between the flanking sequences: Flank 1 (F1 I4L-I5L) and Flank 2 (F2 I4L-I5L). F1rpt stands for a repetitive sequence of Flank 1 to allow deletion of the reporter cassette from a resulting recombinant virus. pBN84 (FIG. 1c) additionally codes for the Denguevirus NS1 protein (NS1 DEN). Further abbreviations: AmpR=Ampicilin resistance gene; bps=base pairs.

Figure 2A:
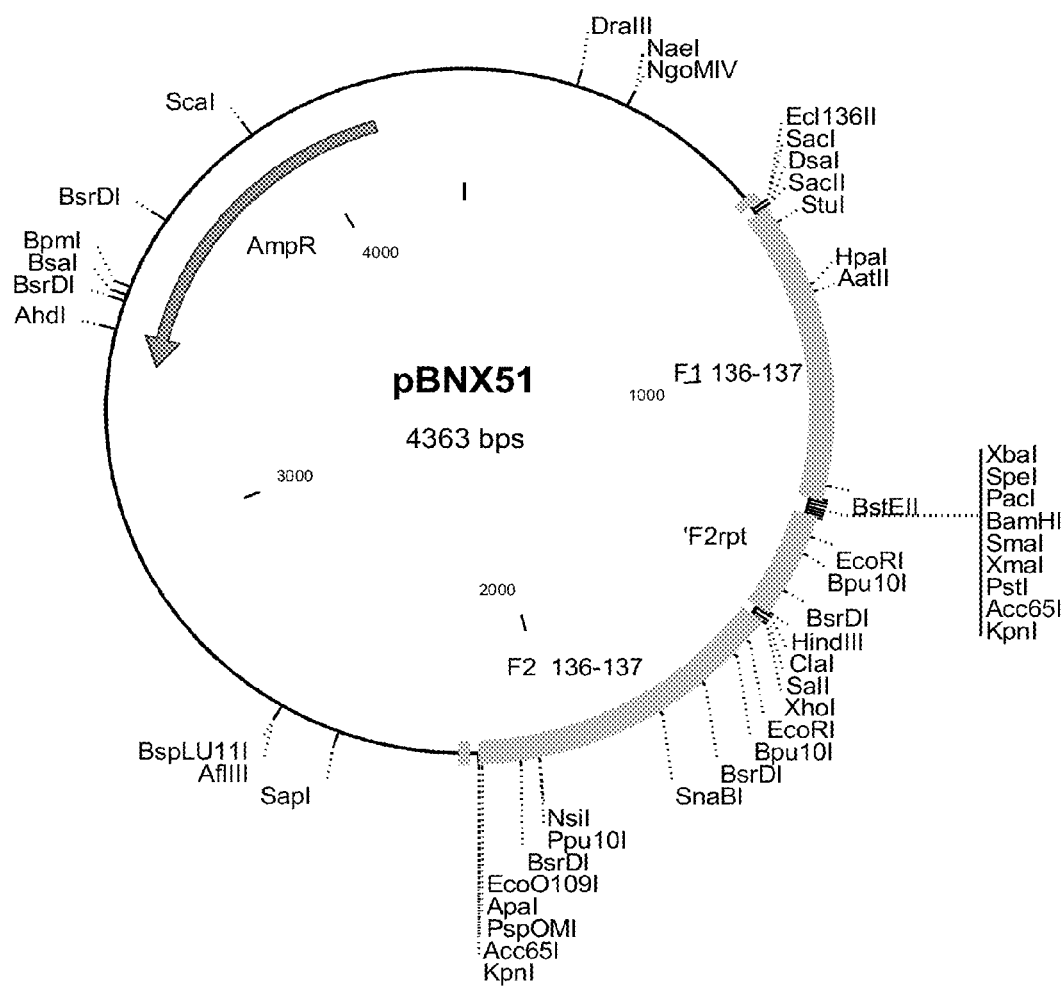
Figure 2B:
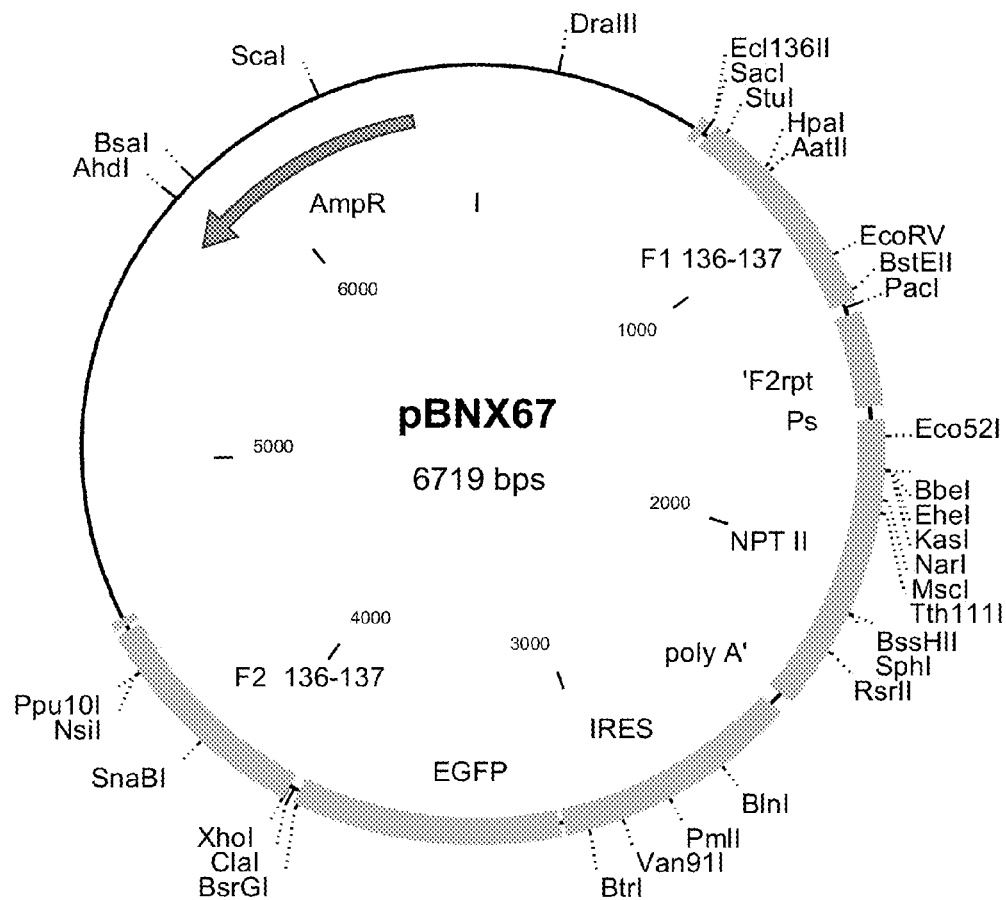
Figure 2C:
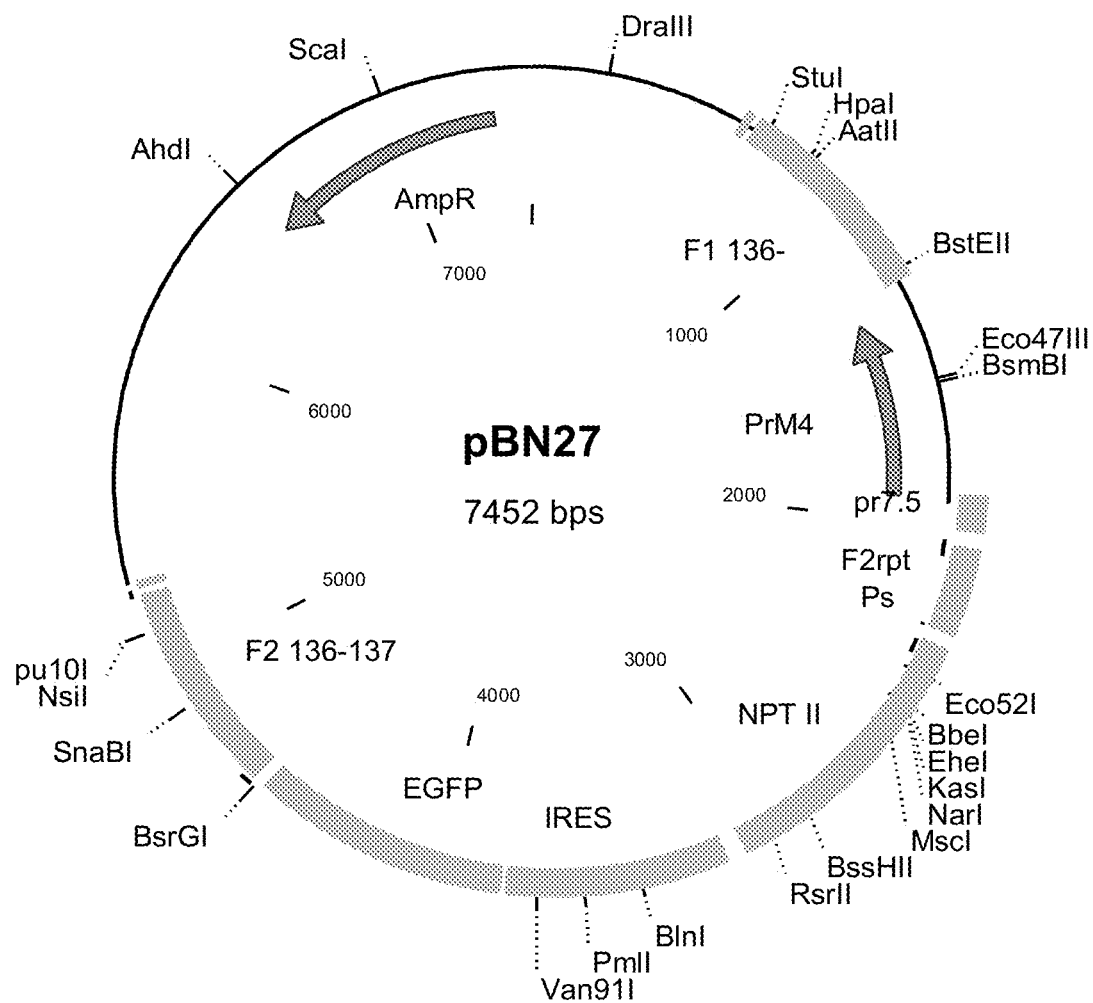
Figure 3A:
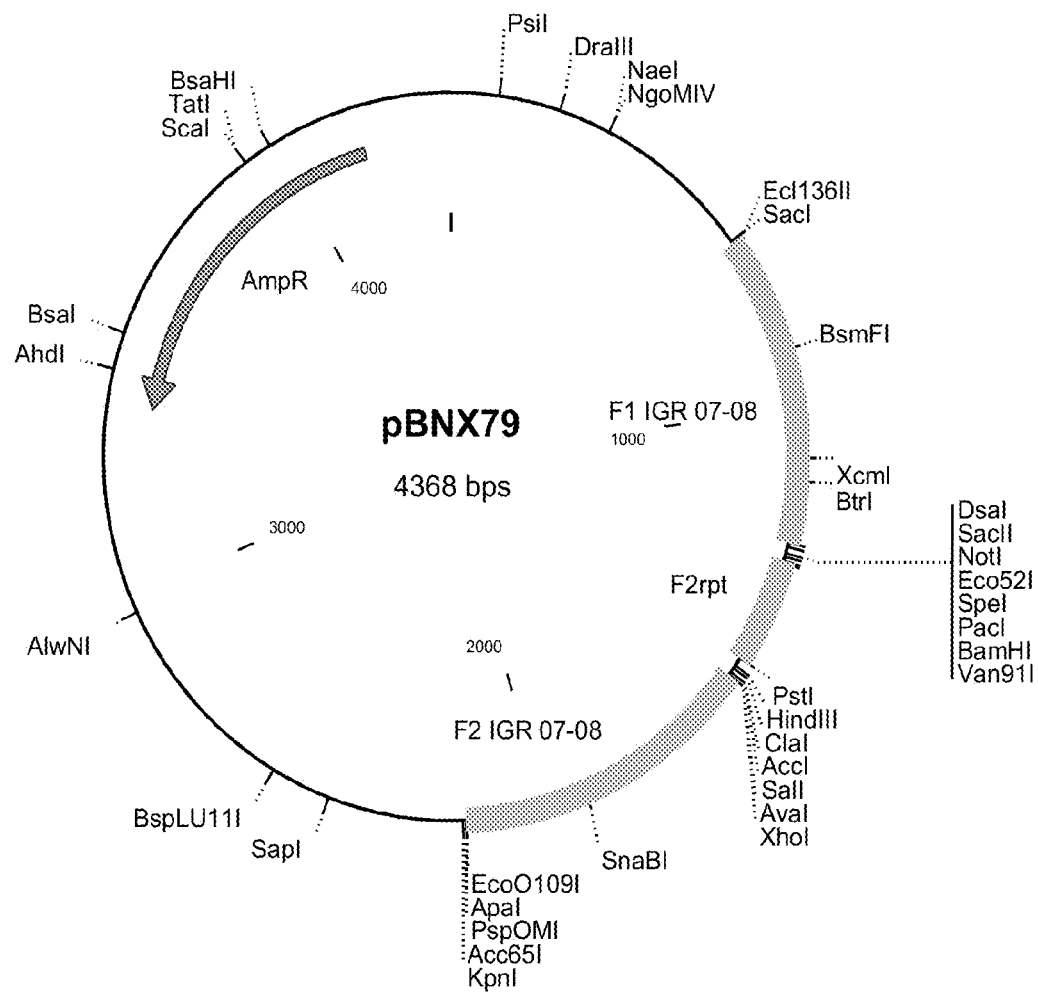
Figure 3B:
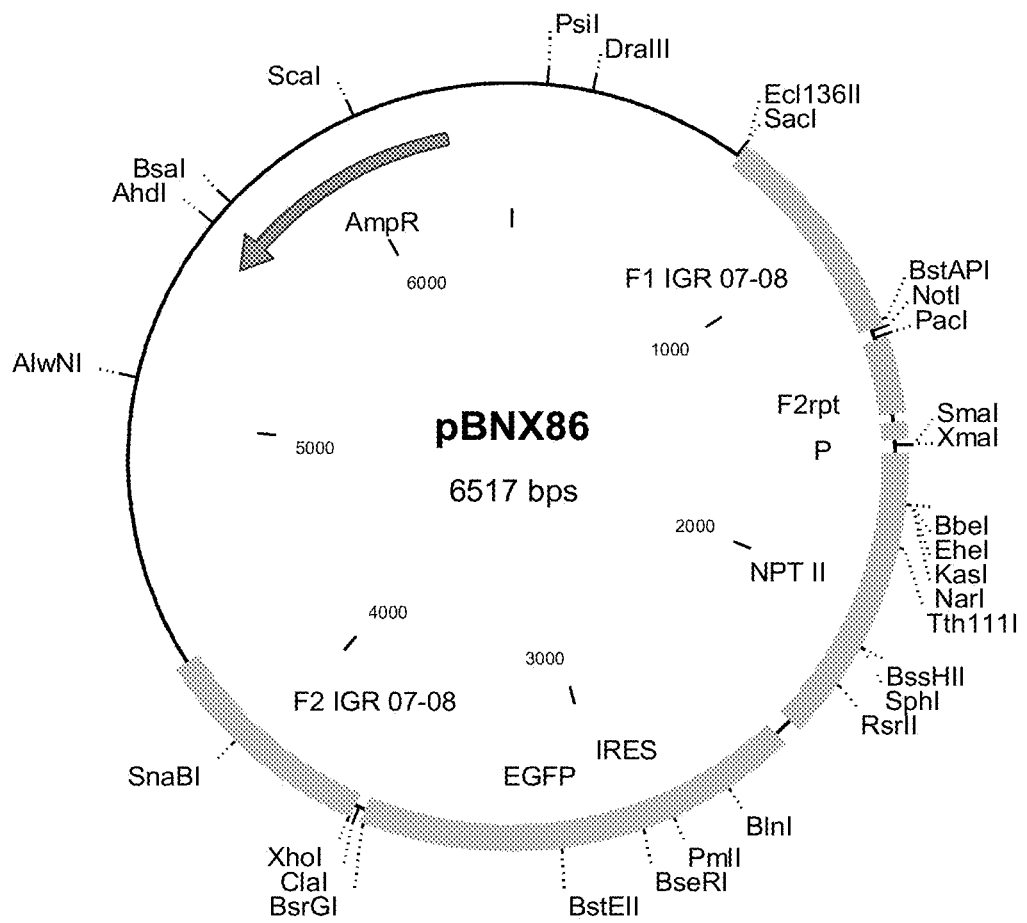
Figure 3C:
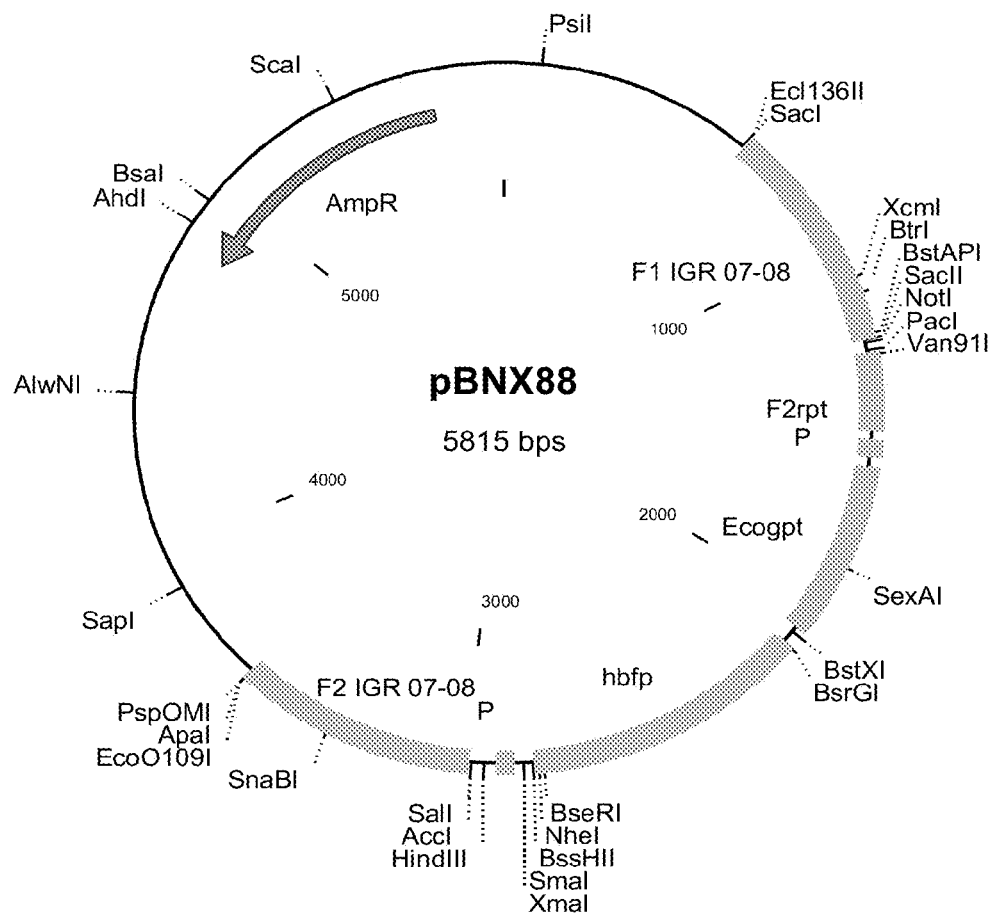
Figure 3D:
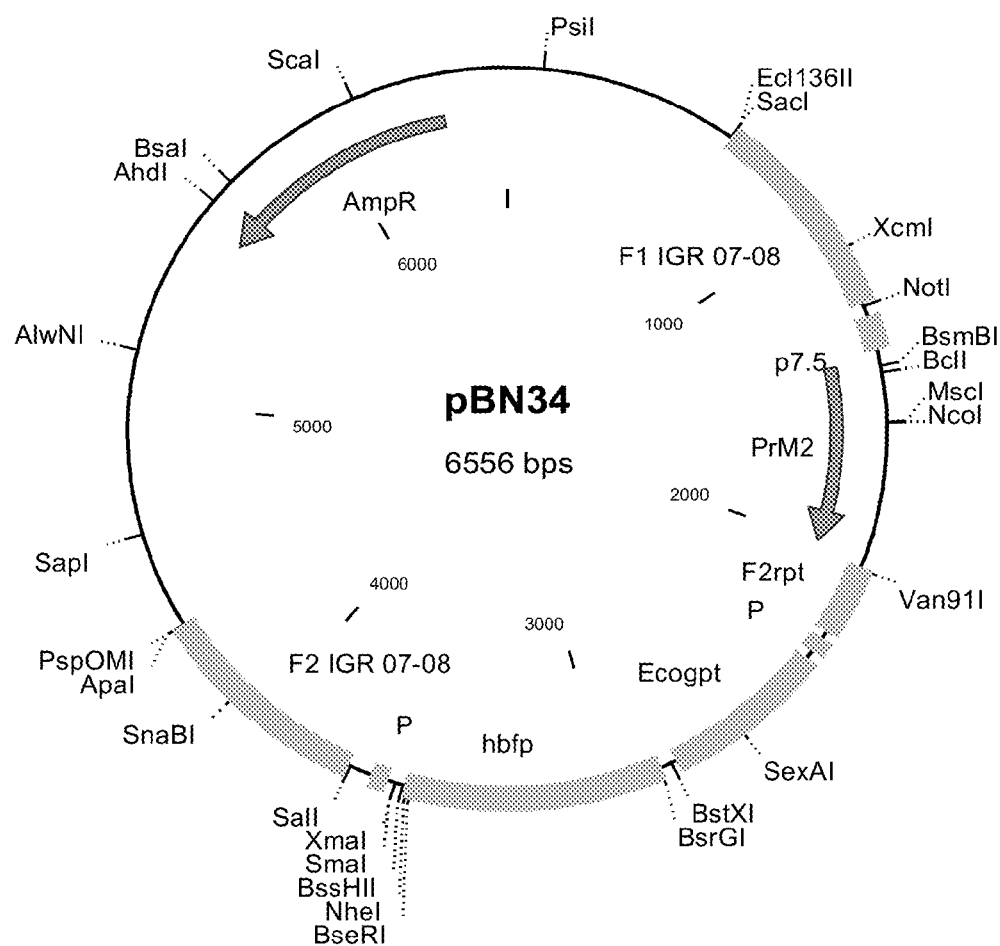
Figure 3E:
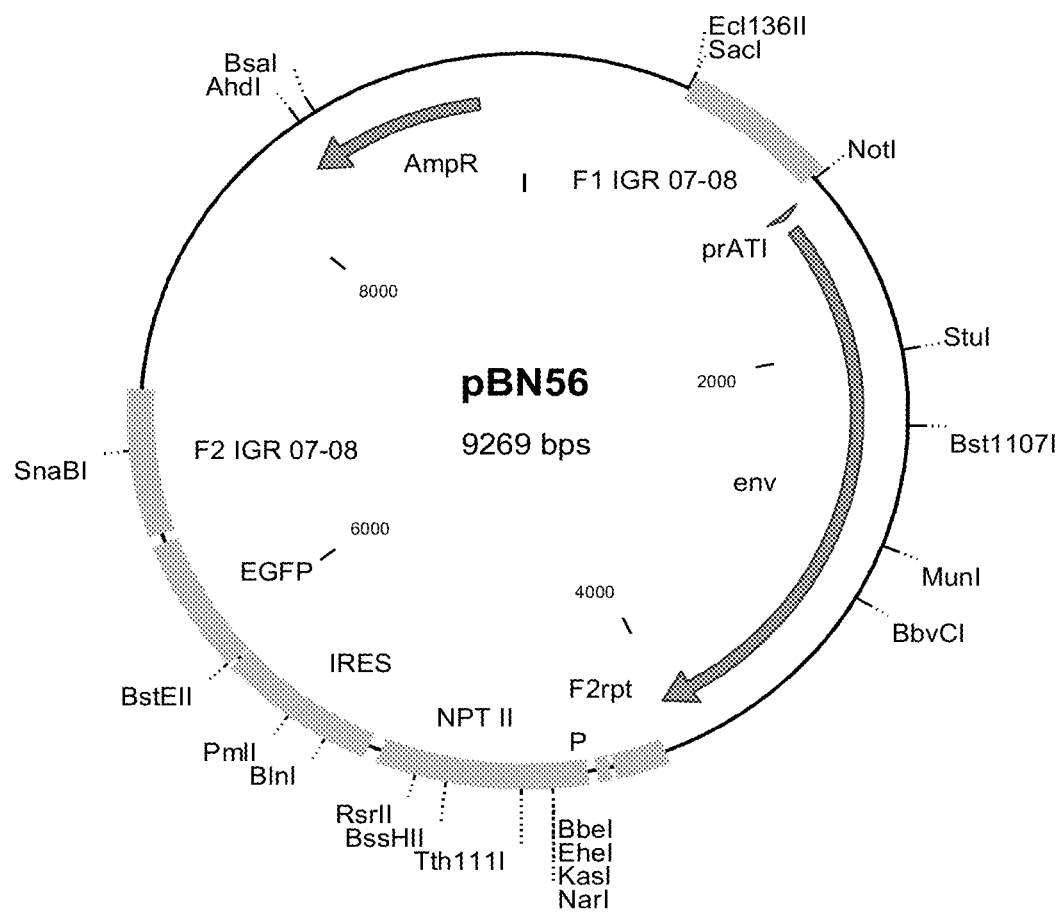

FIG. 2: Restriction map of the vector constructs pBNX51 (FIG. 2a), pBNX67 (FIG. 2b) and pBN27 (FIG. 2c), comprising about 600 bp of MVA sequences flanking the insertion site after the ORF 137L (Flank 1: F1136-137 corresponds to position 129340-129930 of the MVA genome; Flank 2: F2136-137 corresponds to position 129931-130540 of the MVA genome). Additionally the vector pBNX67 (FIG. 2b) comprises exogenous DNA (NPT II gene=neomycin resistance) under the transcriptional control of a poxvirus promoter P) between the flanking sequences. F2rpt stands for a repetitive sequence of Flank 2 to allow deletion of the reporter cassette from a resulting recombinant virus. pBN27 (FIG. 2c) additionally codes for the Denguevirus PrM4 under control of a poxvirus promoter. Further abbreviations: AmpR=Ampicilin resistance gene; bps=base pairs; IRES=internal ribosomal entry site; EGFP=gene for the enhanced green fluorescent protein.

FIG. 3: Restriction map of the vector constructs pBNX79 (FIG. 3a), pBNX86 (FIG. 3b), pBNX88, (FIG. 3c), pBN34 (FIG. 3d) and pBN56 (FIG. 3e), comprising about 600 bps of MVA sequences flanking the insertion site between the ORF 007R and 008L (Flank 1: F1 IGR 07-08 starts at position 12200 of the MVA genome; Flank 2: F2 IGR 07-08 stops at position 13400 of the MVA genome). F2rpt stands for a repetitive sequence of Flank 2 to allow deletion of the reporter cassette from a resulting recombinant virus. Additionally the vector pBNX88 (FIG. 3c) and pBNX86 (FIG. 3b) comprise exogenous DNA (BFP+gpt and NPT II+EGFP, respectively) under the transcriptional control of a poxvirus promoter P) between the flanking sequences. F2rpt stands for a repetitive sequence of Flank 2 to allow deletion of the reporter cassette from a resulting recombinant virus. PBN56 (FIG. 3e) additionally codes for the HIV-1 env protein, and pBN34 (FIG. 3d) contains the Denguevirus PrM2 coding sequence under control of a poxvirus promoter. Further abbreviations: AmpR=Ampicilin resistance gene; bps=base pairs.

Figure 4A:
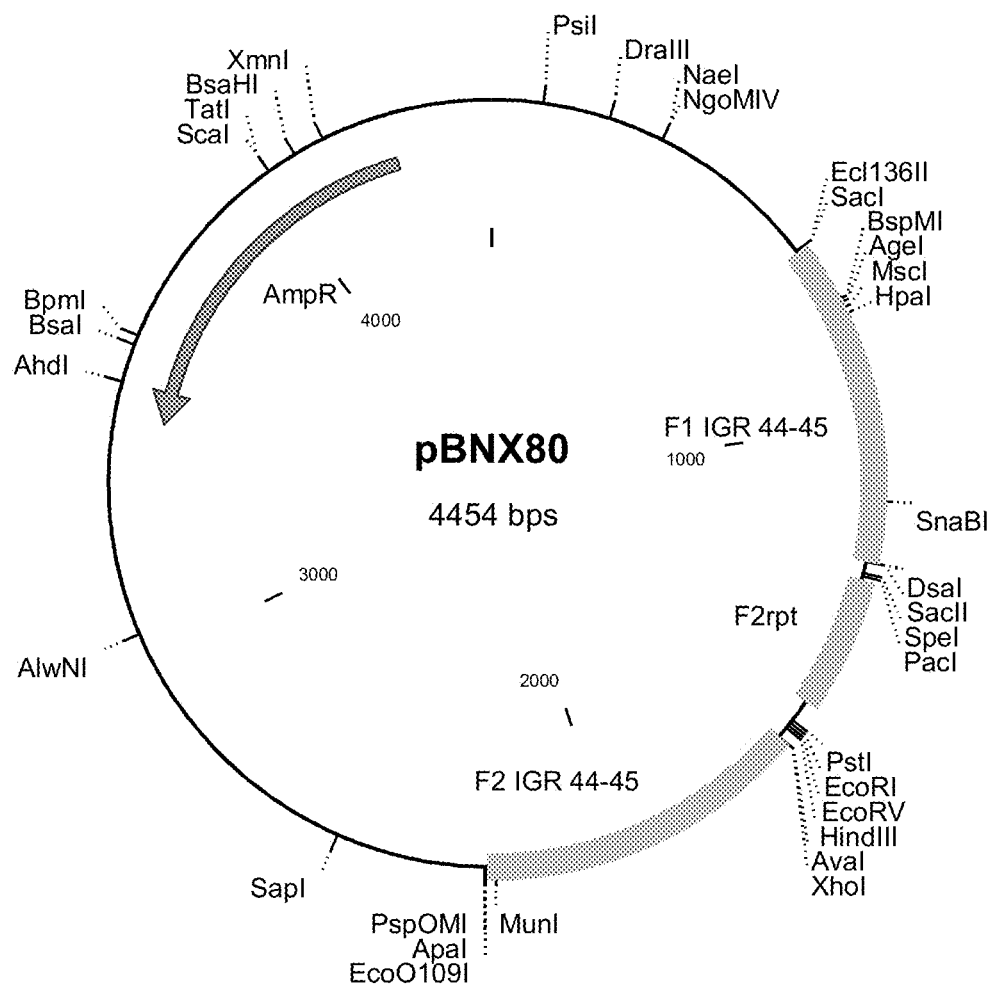
Figure 4B:
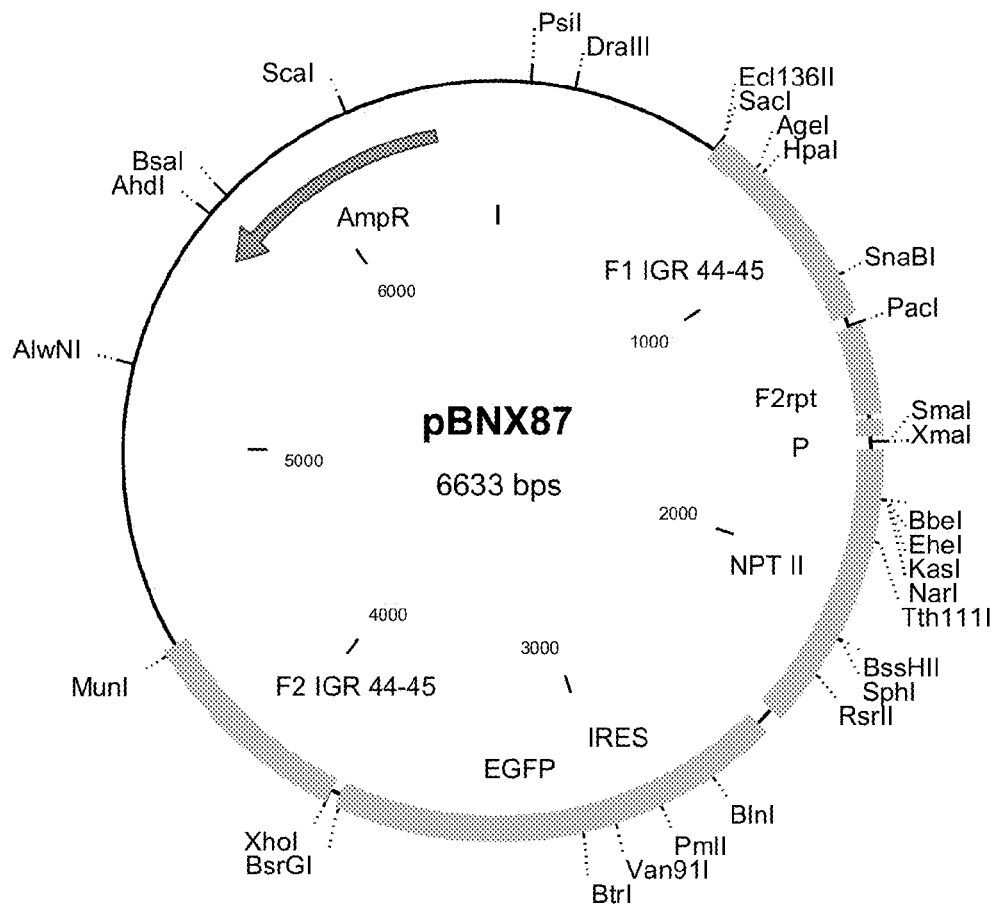
Figure 4C:
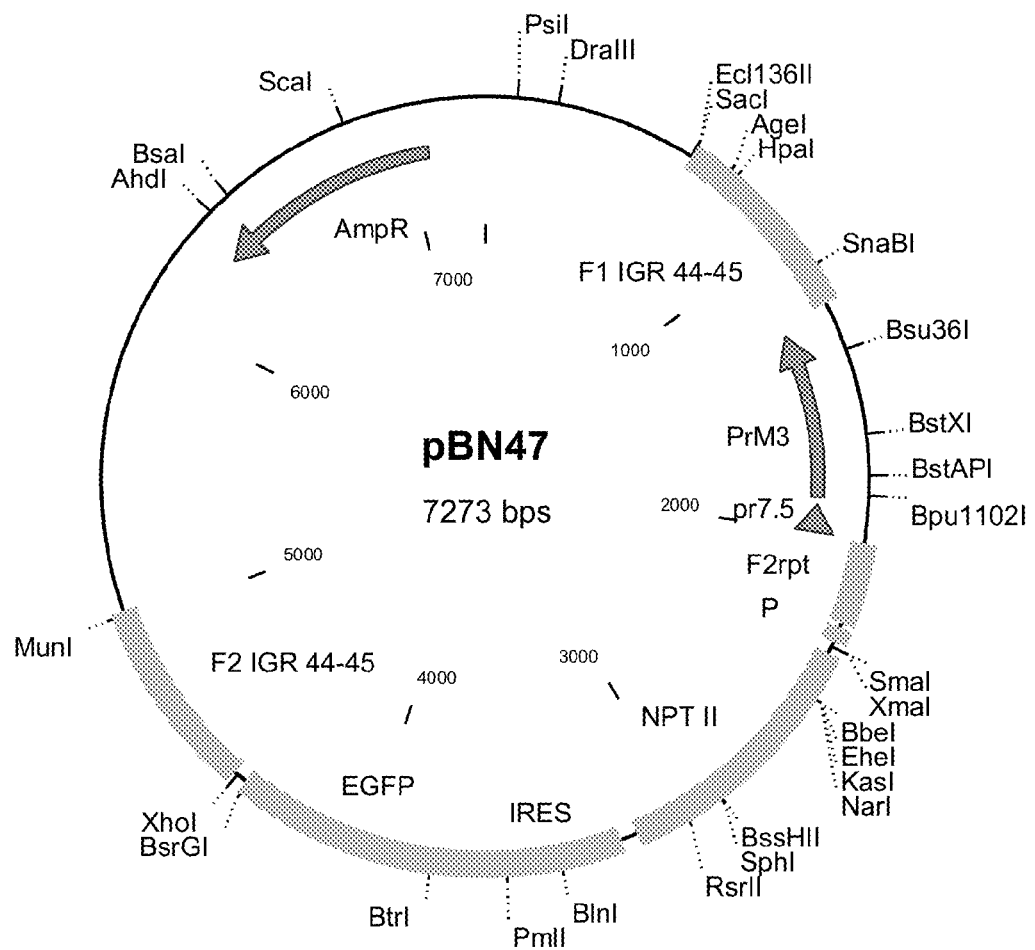

FIG. 4: Restriction map of the vector constructs pBNX80 (FIG. 4a), pBNX87 (FIG. 4b) and pBN47 (FIG. 4c) comprising about 600/640 bps of MVA sequences flanking the insertion site between the ORF 044L and 045L (Flank 1: F1 IGR44-45 starts at position 36730 of the MVA genome; Flank 2: F2 IGR44-45 stops at position 37970 of the MVA genome).

Additionally the vector pBNX87 (FIG. 4b) comprises exogenous DNA (NPT II gene+EGFP) under the transcriptional control of a poxvirus promoter P) between the flanking sequences. F2rpt stands for a repetitive sequence of Flank 2 to allow deletion of the reporter cassette from a resulting recombinant virus. PBN47 (FIG. 4c) additionally codes for the Denguevirus PrM3 under the control of a poxvirus promoter.

Further abbreviations: AmpR=Ampicilin resistance gene; bps=base pairs.

FIG. 5: Restriction map of the vector constructs pBNX90 (FIG. 5*a*), pBNX92 (FIG. 5*b*) and pBN54 (FIG. 5*c*), comprising about 596/604 bps of MVA sequences flanking the insertion site between the ORF 148R and 149L (Flank 1: F1 IGR148-149 starts at position 136900 of the MVA genome; Flank 2: F2 IGR148-149 stops at position 138100 of the MVA genome). Additionally the vector pBNX92 (FIG. 5*b*) comprises exogenous DNA (gpt BFP) under the transcriptional control of a poxvirus promoter P) between the flanking sequences. PBN54 (FIG. 5*c*) additionally codes for the Denguevirus PrM1. F2rpt stands for a repetitive sequence of Flank 2 to allow deletion of the reporter cassette from a resulting recombinant virus. Further abbreviations: AmpR=Ampicilin resistance gene; bps=base pairs.

FIG. 6: Schematic presentation of the intergenic insertion sites of MVA (Genbank Ac. U94848).

FIG. 7: PCR analysis of IGR I4L-I5L in recombinant MVA with the Denguevirus NS1 inserted in the IGR I4L-I5L. Lane "BN" shows the PCR product using MVA-BN empty vector. Using the NS1 recombinant MVA a fragment of bigger size is detectable (1, 2, 3, 4: different concentrations of DNA). M=Molecular weight marker, $H_2O$=water negative control.

FIG. 8: FIG. 8*a*: PCR analysis of IGR 136-137 in recombinant MVA with the Denguevirus PrM4 inserted in the IGR 136-137. Lane "BN" shows the PCR product using MVA-BN empty vector. Using the PrM4 recombinant MVA a fragment of bigger size is detectable (mBN23, 1/10, 1/100: different concentrations of DNA). M=Molecular weight marker, $H_2O$=water negative control, pBN27=plasmid positive control.

FIG. 8*b*: multiple step growth curve for MVA-BN empty vector and the recombinant MVA with PrM4 inserted in IGR 136-137 (MVA-mBN23).

FIG. 9: FIG. 9*a*: PCR analysis of IGR 07-08 in recombinant MVA with the Denguevirus PrM2 inserted in the IGR 07-08. Lane 3 shows the PCR product using MVA-BN empty vector. Using the PrM2 recombinant MVA a fragment of bigger size is detectable (lane 2). M=Molecular weight marker, lane 1=water negative control.

FIG. 9*b*: multiple step growth curve for MVA-BN empty vector and the recombinant MVA with PrM2 inserted in IGR 07-08 (MVA-mBN25).

FIG. 10: PCR analysis of IGR 07-08 in recombinant MVA with the HIV env inserted in the IGR 07-08. Lane BN shows the PCR product using MVA-BN empty vector. Using the PrM2 recombinant MVA a fragment of bigger size is detectable (lane 1, 2, 3). M=Molecular weight marker, −=water negative control, +=plasmid positive control.

FIG. 11: FIG. 11*a*: PCR analysis of IGR 44-45 in recombinant MVA with the Denguevirus PrM3 inserted in the IGR 44-45. Lane BN shows the PCR product using MVA-BN empty vector. Using the PrM3 recombinant MVA a fragment of bigger size is detectable (lane 1-4 different concentrations of DNA). M=Molecular weight marker, −=water negative control.

FIG. 11*b*: multiple step growth curve for MVA-BN empty vector and the recombinant MVA with PrM3 inserted in IGR 44-45 (MVA-mBN28).

FIG. 12: FIG. 12*a*: PCR analysis of IGR 148-149 in recombinant MVA with the Denguevirus PrM1 inserted in the IGR 148-149. Lane BN shows the PCR product using MVA-BN empty vector. Using the PrM1 recombinant MVA a fragment of bigger size is detectable (lane 1). M=Molecular weight marker, −=water negative control, +=plasmid positive control.

FIG. 12*b*: multiple step growth curve for MVA-BN empty vector and the recombinant MVA with PrM1 inserted in IGR 44-45 (MVA-mBN33).

The following examples will further illustrate the present invention. It will be well understood by any person skilled in the art that the provided examples in no way are to be interpreted in a way that limits the present invention to these examples. The scope of the invention is only to be limited by the full scope of the appended claims.

EXAMPLE 1

Insertion Vectors pBNX39, pBNX70 and pBN84

For the insertion of exogenous sequences into the intergenic region adjacent to the 065L ORF (insertion site is at genome position 56760) of MVA, a vector was constructed which comprises about 1200 bp of the flanking sequences adjacent to the insertion site. These flanking sequence are separated into two flanks comprising on one flank about 610 bp of the 065L ORF (alternative nomenclature: I4L ORF) and on the other part about 580 bp of the intergenic region behind the 065L ORF as well as parts of the proximate ORF. In between these flanking sequences an Ecogpt gene (gpt stands for phosphoribosyltransferase gene isolated from *E. coli*) and a BFP (blue fluorescence protein), respectively, is located under the transcriptional control of a poxviral promoter. Additionally, there is at least one cloning site for the insertion of additional genes or sequences to be inserted into the intergenic region behind the I4L ORF. Exemplary vector constructs according to the present invention are disclosed in FIG. 1 *a*) and *b*) (pBNX39, pBNX70). In vector pBN84 (FIG. 1*c*) the coding region for Denguevirus NS1 is inserted in the cloning site of pBNX70 (FIG. 1*b*).

Generation of the Recombinant MVA Via Homologous Recombination

Foreign genes can be inserted into the MVA genome by homologous recombination. For that purpose the foreign gene of interest is cloned into a plasmid vector, as described above. This vector is transfected in MVA infected cells. The recombination takes place in the cytoplasm of the infected and transfected cells. With help of the selection and/or reporter cassette, which is also contained in the insertion vector, cells comprising recombinant viruses are identified and isolated.

For homologous recombination BHK (Baby hamster kidney) cells or CEF (primary chicken embryo fibroblasts) are seeded in 6 well plates using DMEM (Dulbecco's Modified Eagles Medium, Gibco BRL)+10% fetal calf serum (FCS) or VP-SFM (Gibco BRL)+4 mmol/l L-Glutamine for a serum free production process.

Cells need to be still in the growing phase and therefore should reach 60-80% confluence on the day of transfection. Cells were counted before seeding, as the number of cells has to be known for determination of the multiplicity of infection (moi) for infection.

For the infection the MVA stock is diluted in DMEM/FCS or VP-SFM/L-Glutamine so that 500 µl dilution contain an appropriate amount of virus that will give a moi of 0.1-1.0.

Cells are assumed to have divided once after seeding. The medium is removed from cells and cells are infected with 500 µl of diluted virus for 1 hour rocking at room temperature. The inoculum is removed and cells are washed with DMEM/VP-SFM. Infected cells are left in 1.6 ml DMEM/FCS and VP-SFM/L-Glutamine, respectively, while setting up the transfection reaction (Qiagen Effectene Kit).

For the transfection, the "Effectene" transfection kit (Qiagen) is used. A transfection mix is prepared of 1-2 µg of linearized insertion vector (total amount for multiple transfection) with buffer EC to give a final volume of 100 µl. Add 3.2 µl Enhancer, vortex and incubate at room temperature for 5 min. Then, 10 µl of Effectene are added after vortexing stock tube and the solution is mixed thoroughly by vortexing and incubated at room temperature for 10 min. 600 µl of DMEM/FCS and VP-SFM/L-Glutamine respectively, are added, mixed and subsequently, the whole transfection mix is added to the cells, which are already covered with medium. Gently the dish is rocked to mix the transfection reaction. Incubation takes place at 37° C. with 5% $CO_2$ over night. The next day the medium is removed and replaced with fresh DMEM/FCS or VP-SFM/L-Glutamine. Incubation is continued until day 3.

For harvesting, the cells are scraped into medium, then the cell suspension is transferred to an adequate tube and frozen at −20° C. for short-term storage or at −80° C. for long-term storage.

Insertion of Ecogpt in the I4L Insertion Site of MVA

In a first round, cells were infected with MVA according to the above-described protocol and were additionally transfected with insertion vector pBNX39 (FIG. 1a) containing the Ecogpt gene (Ecogpt, or shortened to gpt, stands for phosphoribosyltransferase gene) as reporter gene. Resulting recombinant viruses were purified by 3 rounds of plaque purification under phosphribosyl-transferase metabolism selection by addition of mycophenolic acid, xanthin and hypoxanthin. Mycophenolic acid (MPA) inhibits inosine monophosphate dehydrogenase and results in blockage of purine synthesis and inhibition of viral replication in most cell lines. This blockage can be overcome by expressing Ecogpt from a constitutive promoter and providing the substrates xanthine and hypoxanthine.

Resulting recombinant viruses were identified by standard PCR assays using a primer pair selectively amplifying the expected insertion site. To amplify the I4L insertion side primer pair, BN499 (CAA CTC TCT TCT TGA TTA CC, SEQ ID NO.: 1) and BN500 (CGA TCA AAG TCA ATC TAT G, SEQ ID NO.: 2) were used. In case the DNA of the empty vector virus MVA is amplified the expected PCR fragment is 328 nucleotides (nt) long, in case a recombinant MVA is amplified, which has incorporated exogenous DNA at the I4L insertion site, the fragment is correspondingly enlarged.

Insertion of NS1 in the IGRO64L-065L (I4L-I5L) Insertion Site of MVA

In a first round, cells were infected with MVA according to the above-described protocol and were additionally transfected with insertion vector pBN84 (FIG. 1c) containing the Ecogpt gene for selection and BFP (Blue fluorescence protein) as reporter gene. Resulting recombinant viruses were purified by 7 rounds of plaque purification under phosphribosyl-transferase metabolism selection by addition of mycophenolic acid, xanthin and hypoxanthin. Mycophenolic acid (MPA) inhibits inosine monophosphate dehydrogenase and results in blockage of purine synthesis and inhibition of viral replication in most cell lines. This blockage can be overcome by expressing Ecogpt from a constitutive promoter and providing the substrates xanthine and hypoxanthine.

Figure 7:
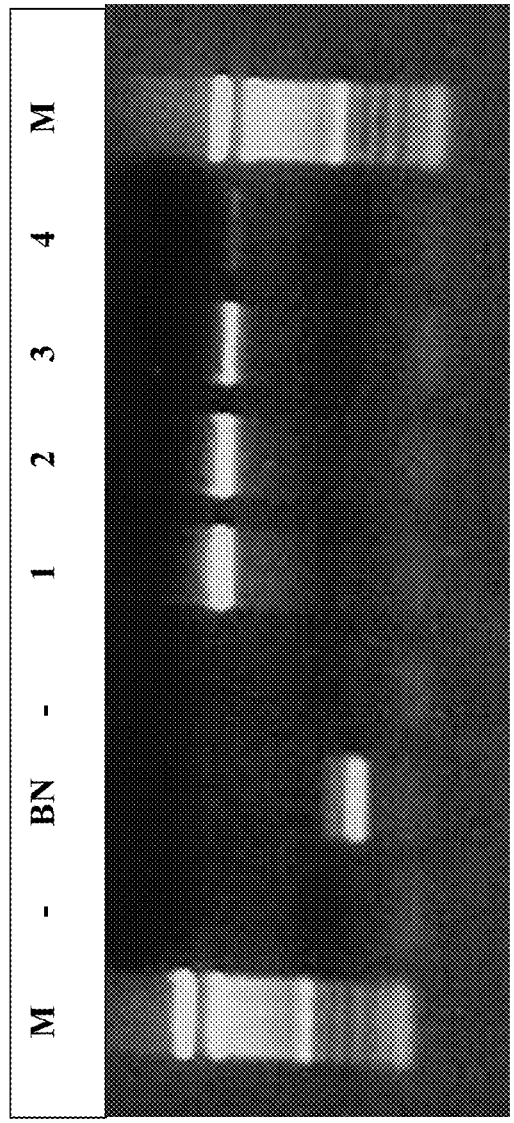
Figure 8A:
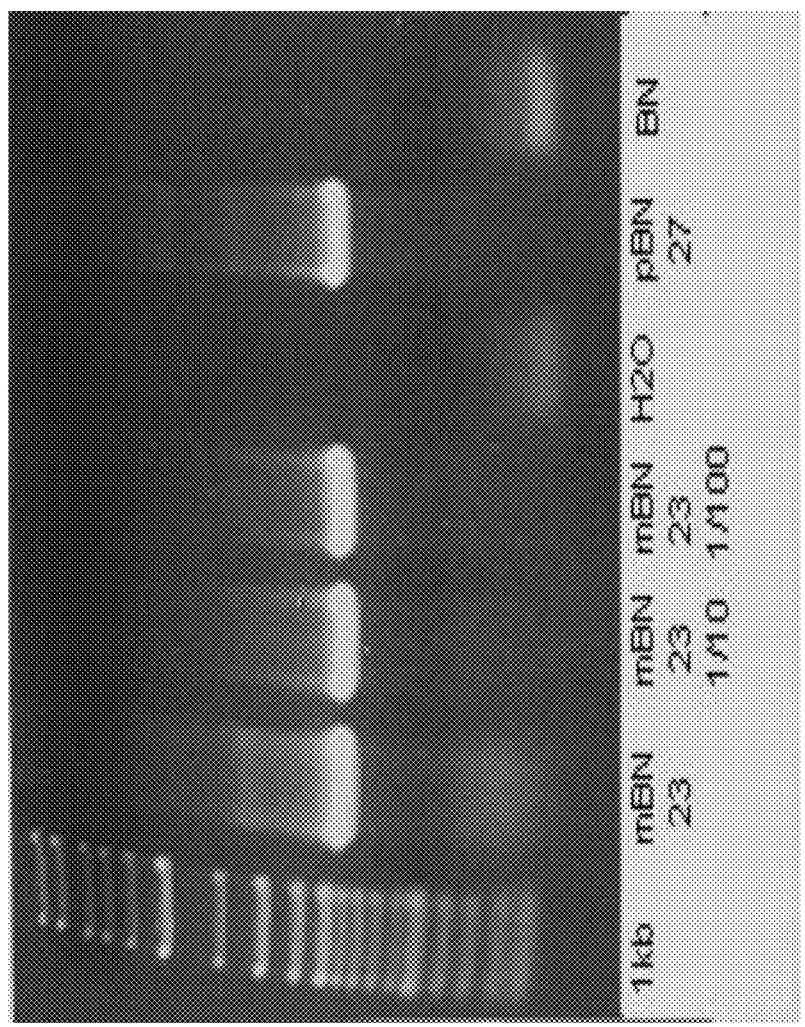
Figure 8B:
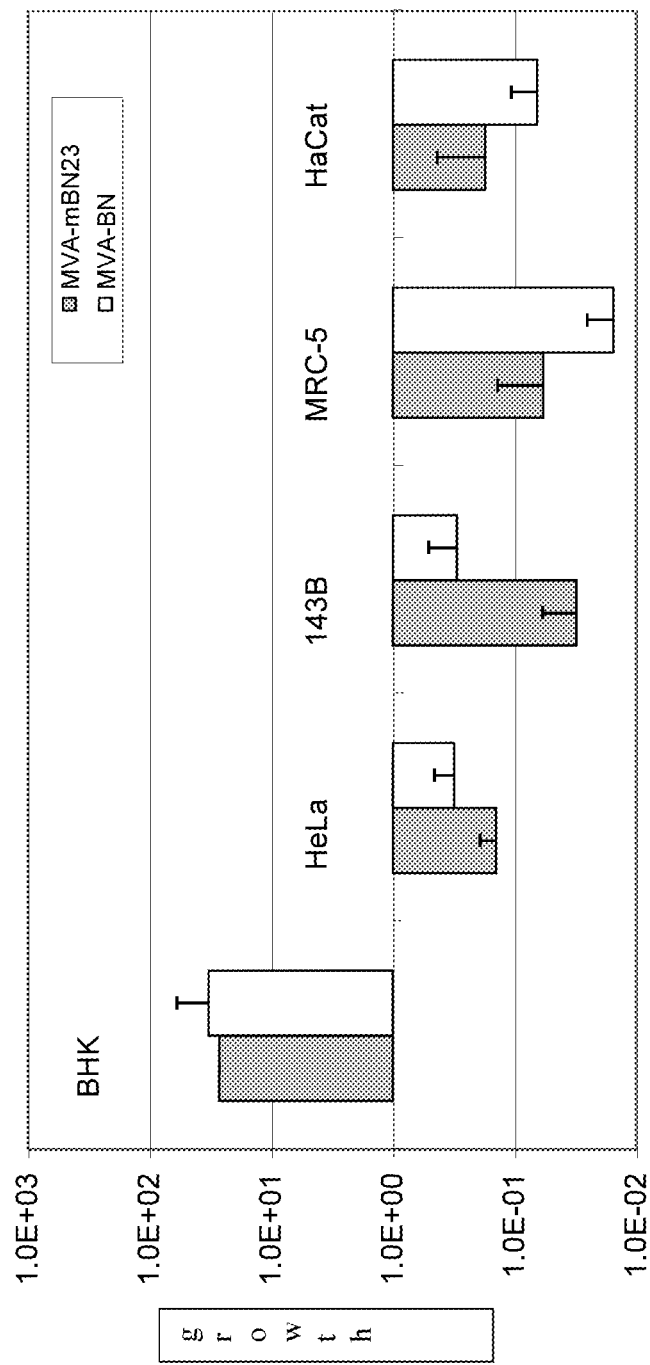

Resulting recombinant viruses were identified by standard PCR assays using a primer pair selectively amplifying the expected insertion site. To amplify the I4L insertion side primer pair, BN499 (CAA CTC TCT TCT TGA TTA CC, SEQ ID NO.: 1) and BN500 (CGA TCA AAG TCA ATC TAT G, SEQ ID NO.: 2) were used. In case the DNA of the empty vector virus MVA is amplified the expected PCR fragment is 328 nucleotides (nt) long, in case a recombinant MVA for NS1 is amplified, which has incorporated Denguevirus NS1 coding region at the I4L insertion site, the fragment is expected to be 1683 bp. The PCR results in FIG. 7 show clearly the stable insertion of NS1 in the I4L insertion site after 17 rounds of virus amplification.

Testing of recMVA Including NS1 (MVA-BN22) In Vitro

A T25 flask with about 80% confluent monolayers of BHK cells was inoculated with 100 µl of the virus stock diluted to $1 \times 10^7$ in MEMa with 1% FCS and rocked at room temperature for 30 minutes. 5 ml of MEMa with 3% FCS was added to each flask and incubated at 30° C. in a $CO_2$ incubator. The flask was harvested after 48 hours. The supernatant was removed from the flask and spun at 260 g for 10 minutes at 4° C. The supernatants were stored in aliquots at −80° C. The pellet was washed with 5 ml of 1×PBS twice and then resuspended in 1 ml of hypotonic douncing buffer with 1% TX100. The cell lysates were harvested and spun for 5 minutes at 16,000 g and the supernatants were stored in a microcentrifuges tube at −80° C.

Flasks inoculated with MVA including GFP, MVA including the NS1 gene in a deletion site (MVA-BN07), and mock infected flasks were also treated the same way as described above.

The cell/viral lysate and the supernatant were treated in non-reducing/reducing sample buffer under non-heated/heated conditions. The proteins were separated on 10% SDS PAGE and transferred to nitrocellulose membranes. The blots were probed overnight with pooled convalescent patients' sera (PPCS) at 1:500 dilution. After washing 3 times with 1×PBS the blots were incubated with anti-human IgG-HRP (DAKO) for 2 hours at room temperature. After the blots were washed as described before, the colour was developed using 4 chloro-1-naphthol.

The western blot results showed that NS1 in MVA-BN22 is expressed in large quantities. NS1 was expressed in the right confirmation, as a dimer under non-heated condition and as a monomer under heated condition.

The NS1 expression was compared in both MVA-BN22 and MVA-BN07. The BHK cells were inoculated with the same pfu and harvested after 48 hours. The results showed that the expression of NS1 was much higher in BN22 than in BN07. The western blots results also showed that there is more NS1 secreted in the supernatant with the BN22 construct compared to BN07.

The results also showed that NS1 expressed in cells infected with BN22 is antigenic and is recognized by the pooled convalescent patients' sera.

In conclusion, NS1 is expressed in large quantities and in the right confirmation in the BHK cells infected with BN22. Both the dimer and monomer are antigenic and are recognized by the pooled convalescent patients' sera.

EXAMPLE 2

Insertion Vector pBNX67 and pBN27

The MVA sequences adjacent the new insertion site (at genome position 129940) between the ORF 136L and 137L were isolated by standard PCR amplification of the sequence of interest using the following primers:

oBN543 (TCCCCGCGGAGAGGCGTAAAAGT-TAAATTAGAT; SEQ ID NO.: 3) and oBN544 (TGATCTA-GAATCGCTCGTAAAAACTGCGGAGGT;

SEQ ID NO.: 4) for isolating Flank 1;

oBN578 (CCGCTCGAGTTCACGTTCAGCCT-TCATGC; SEQ ID NO.: 5) and oBN579 (CGGGGGC-CCTATTTTGTATAATATCTGGTAAG; SEQ ID NO.: 6) for isolating Flank 2.

The PCR fragment comprising Flank 1 was treated with the restriction enzymes SacII and XbaI and ligated to, a SacII/XbaI digested and dephosphorylated basic vector, such as pBluescript (Stratagene).

The resulting plasmid was XhoI/ApaI digested, dephosphorylated and ligated to the XhoI/ApaI digested PCR fragment comprising Flank 2.

Optionally, a repetitive sequence of Flank 2 which had been isolated by PCR using the primers oBN545 (CGGCT-GCAGGGTACCTTCACGTTCAGCCTTCATGC; SEQ ID NO.: 7) and oBN546 (CGGAAGCTTTATATGGTTTAG-GATATTCTGTTTT; SEQ ID NO.: 8) and which became HindIII/PstI digested, was inserted into the HindIII/PstI site of the resulting vector. FIG. 2a) shows the vector (pBNX51).

A reporter cassette comprising a synthetic promoter, NPT II gene (neomycin resistance), poly-A region, IRES, EGFP gene (Ps-NPTII-polyA-IRES-EGFP) was Ecl136II/XhoI digested and inserted into the HindIII/XhoI site of the insertion vector, wherein the HindIII site was blunt ended with T4 DNA Polymerase (Roche). A restriction map of an exemplary vector construct according to this example is disclosed in FIG. 2b) (pBNX67).

For construction of pBN27 (FIG. 2c) the Denguevirus PrM of serotype 4 was inserted in the single PacI site of pBNX67.
Generation of the Recombinant MVA Via Homologous Recombination The vector pBNX67 (FIG. 2*b*) can be used to generate a recombinant MVA using the above mentioned protocol—e.g. using pBN27 (FIG. 2*c*) for homologous recombination results in a recombinant MVA carrying Denguevirus PrM4 in the intergenic region between two adjacent ORFs.

Insertion of PrM4 in the IGR136-137 Insertion Site of MVA

In a first round, cells were infected with MVA according to the above-described protocol and were additionally transfected with insertion vector pBN27 (FIG. 2*c*) containing the NPT gene for selection and EGFP (enhanced green fluorescence protein) as reporter gene. Resulting recombinant viruses were purified by 4 rounds of plaque purification under G418 selection.

Resulting recombinant viruses were identified by standard PCR assays using a primer pair selectively amplifying the expected insertion site. To amplify the IGR136-137 insertion side primer pair, BN900 (cgttcgcatgggttacctcc, SEQ ID NO.: 9) and BN901 (gacgcatgaaggctgaac, SEQ ID NO.: 10) were used. In case the DNA of the empty vector virus MVA is amplified the expected PCR fragment is 88 nucleotides (nt) long, in case a recombinant MVA for PrM4 is amplified, which has incorporated Denguevirus PrM4 coding region at the IGR136-137 insertion site, the fragment is expected to be 880 bp. The PCR results in FIG. 8*a*) show clearly the stable insertion of PrM4 in the IGR136-137 insertion site after 22 rounds of virus amplification. The recombinant MVA still shows the same growth characteristics as MVA-BN. It replicates in chicken embryo fibroblasts (CEF cells) and grows attenuated in mammalian cells (FIG. 8*b*).

EXAMPLE 3

Insertion Vector pBNX79, pBNX86, pBNX88, pBN34 and pBN56

The MVA sequences adjacent the new insertion site (at genome position 12800) between the ORF 007R and 008L were isolated by standard PCR amplification of the sequence of interest using the following primers:

IGR 07/08 F1up (CGCGAGCTCAATAAAAAAAAGTTTTAC; SEQ ID NO.: 11) and IGR 07/08 F1end (AGGCCGCGGATGCATGTTATGCAAAATAT;

SEQ ID NO.: 12) for isolating Flank 1;

IGR 07/08 F2up (CCGCTCGAGCGCGGATCCCAATATATGGCATAGAAC; SEQ ID NO.: 13) and IGR 07/08 F2end (CAGGGCCCTCTCATCGCTTTCATG; SEQ ID NO.: 14) for isolating Flank 2.

The PCR fragment comprising Flank 1 was treated with the restriction enzymes SacII and SacI and ligated to a SacII/SacI digested and dephosphorylated basic vector, such as pBluescript (Stratagene).

The resulting plasmid was XhoI/ApaI digested, dephosphorylated and ligated to the XhoI/ApaI digested PCR fragment comprising Flank 2.

Optionally, a repetitive sequence of Flank 2 which had been isolated by PCR using the primers IGR 07/08 F2up (CCGCTCGAGCGCGGATCCCAATATATGGCATAGAAC; SEQ ID NO.: 13) and IGR 07/08 F2mid (TTTCTGCAGTGATATTTATCCAATACTA; SEQ ID NO.: 15) and which is BamHI/PstI digested, was inserted into the BamHI/PstI site of the resulting vector.

Any reporter or therapeutical gene comprising cassette, having e.g. a poxviral promoter, a marker gene, a poly-A region and optionally an IRES element, a further gene, e.g. expressing a therapeutically active substance or gene product, can be blunt ended with T4 DNA Polymerase (Roche) after a restriction digest and inserted into a suitable cloning site of the plasmid vector. A restriction map of an exemplary vector construct according to this example is disclosed in FIG. 3*a*) (pBNX79). Insertion of the NPT/EGFP selection cassette resulted in vector pBNX86 (FIG. 3*b*) and insertion of the gpt/BFP selection cassette in vector pBNX88 (FIG. 3*c*), respectively. Considering an expression unit for a therapeutic gene, comprising a therapeutic gene and an operably linked promoter, this expression unit is inserted into the Pad site. For construction of pBN34 (FIG. 3*d*) the Denguevirus PrM2 was cloned in pBNX88 (FIG. 3*c*) and for synthesis of pBN56 (FIG. 3*e*) the HIV env coding region was Pad cloned in pBNX86 (FIG. 3*b*).

Generation of the Recombinant MVA Via Homologous Recombination

The vectors pBNX86 (FIG. 3*b*) and pBNX88 (FIG. 3*c*), respectively, can be used to generate a recombinant MVA using the above mentioned protocol. Using pBN34 (FIG. 3*d*) for homologous recombination results in a recombinant MVA carrying Denguevirus PrM2 in the intergenic region between two adjacent ORFs. Recombination of pBN56 (FIG. 3*e*) with the MVA-BN genome results in a recombinant MVA, which contains the HIV env gene in the corresponding IGR.

Insertion of PrM2 in the IGR07-08 Insertion Site of MVA

In a first round, cells were infected with MVA according to the above-described protocol and were additionally transfected with insertion vector pBN34 (FIG. 3*d*) containing the gpt gene for selection and BFP as reporter gene. Resulting recombinant viruses were purified by 3 rounds of plaque purification under selection by mycophenolic acid as described in Example 1.

Figure 9A:
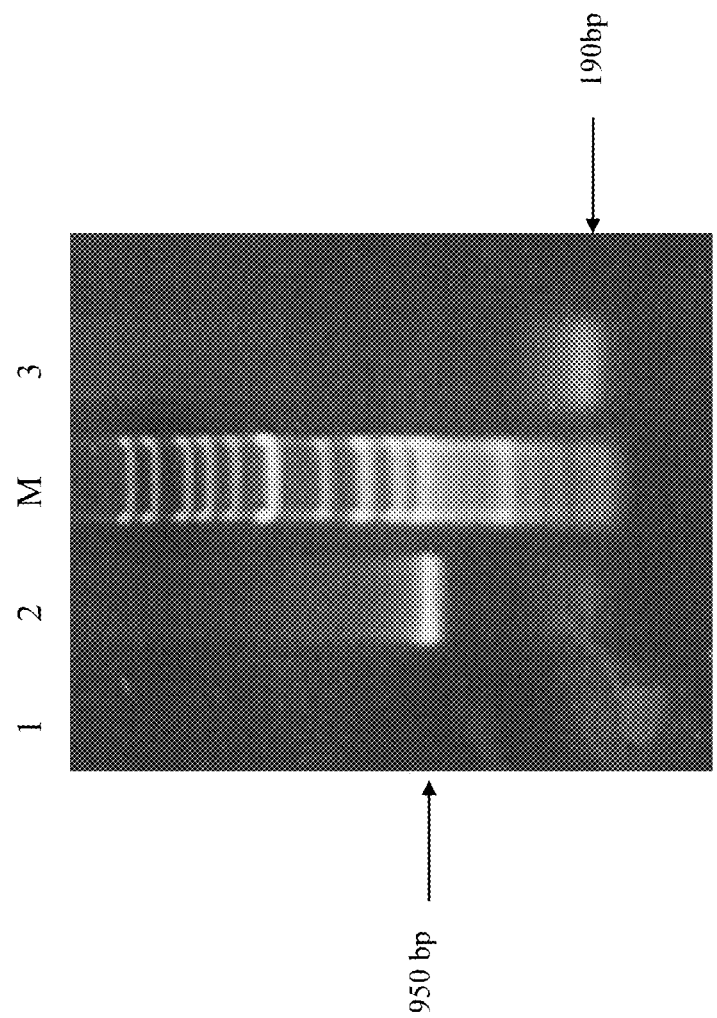
Figure 9B:
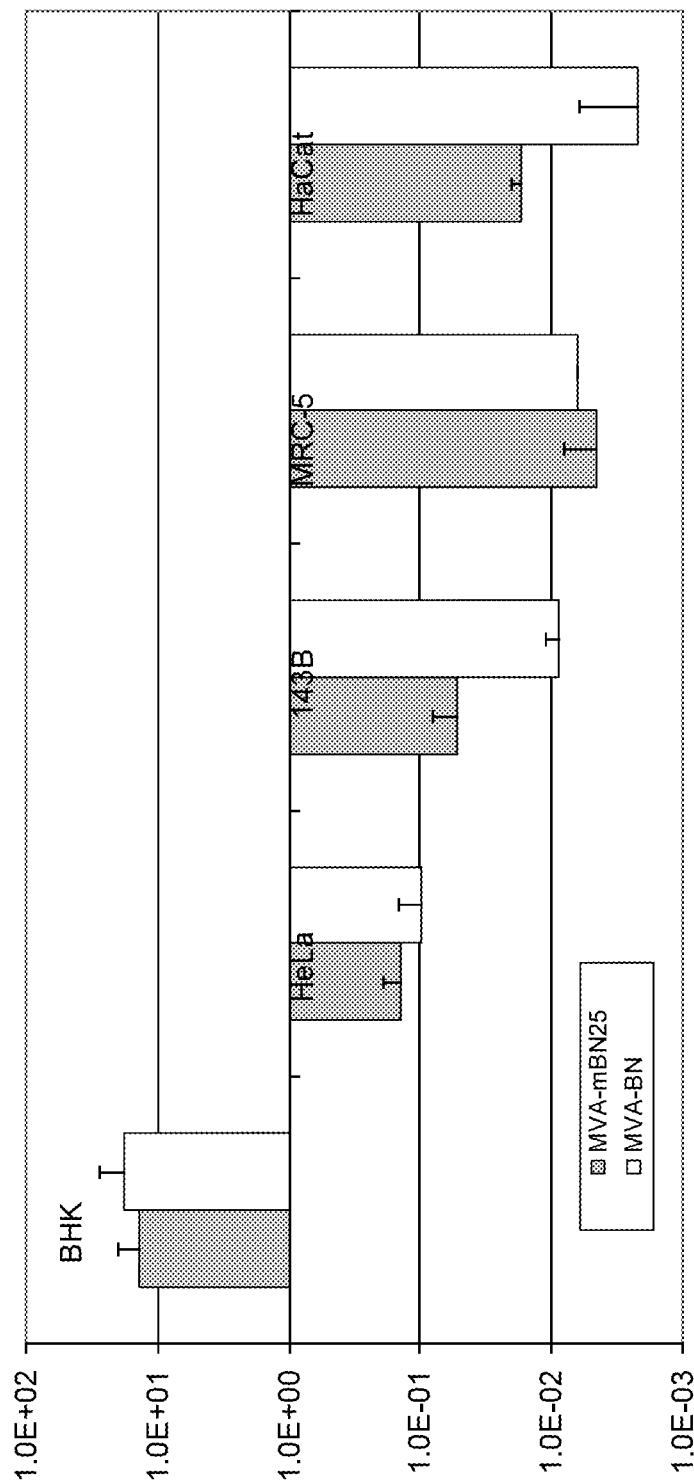
Figure 10:
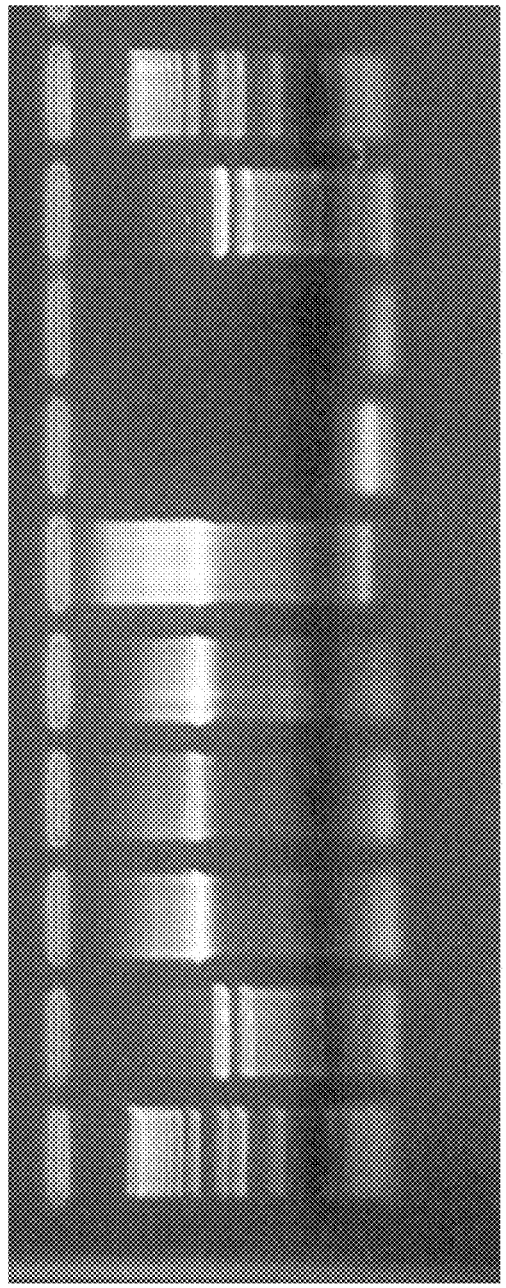
Figure 11A:
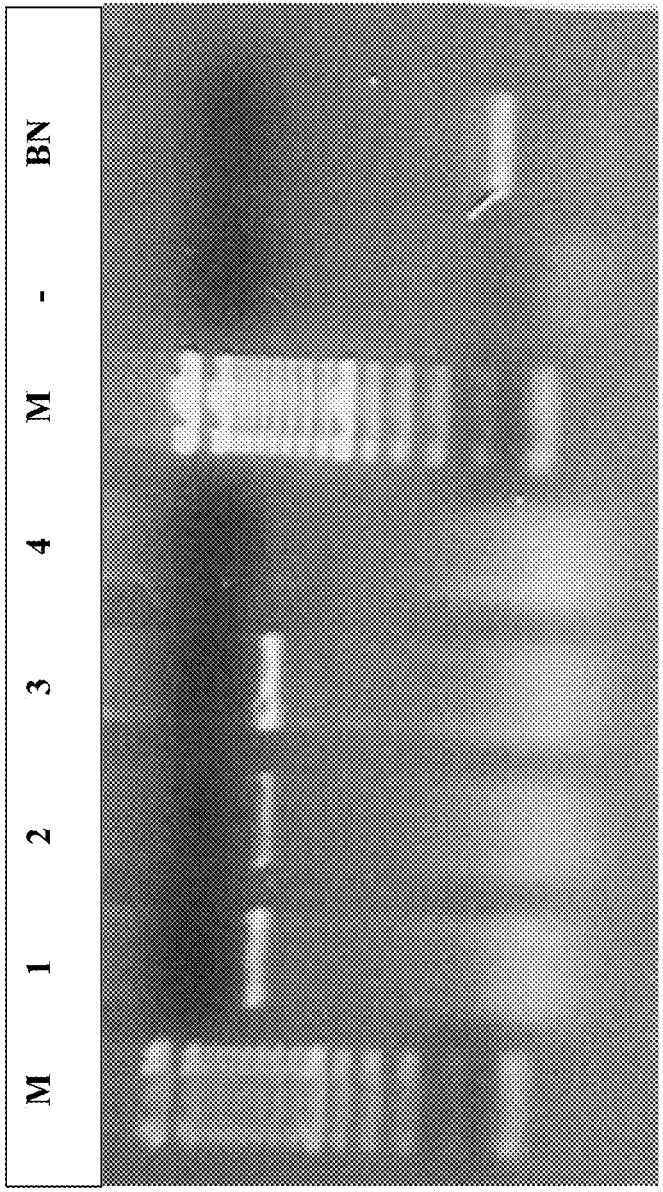
Figure 11B:
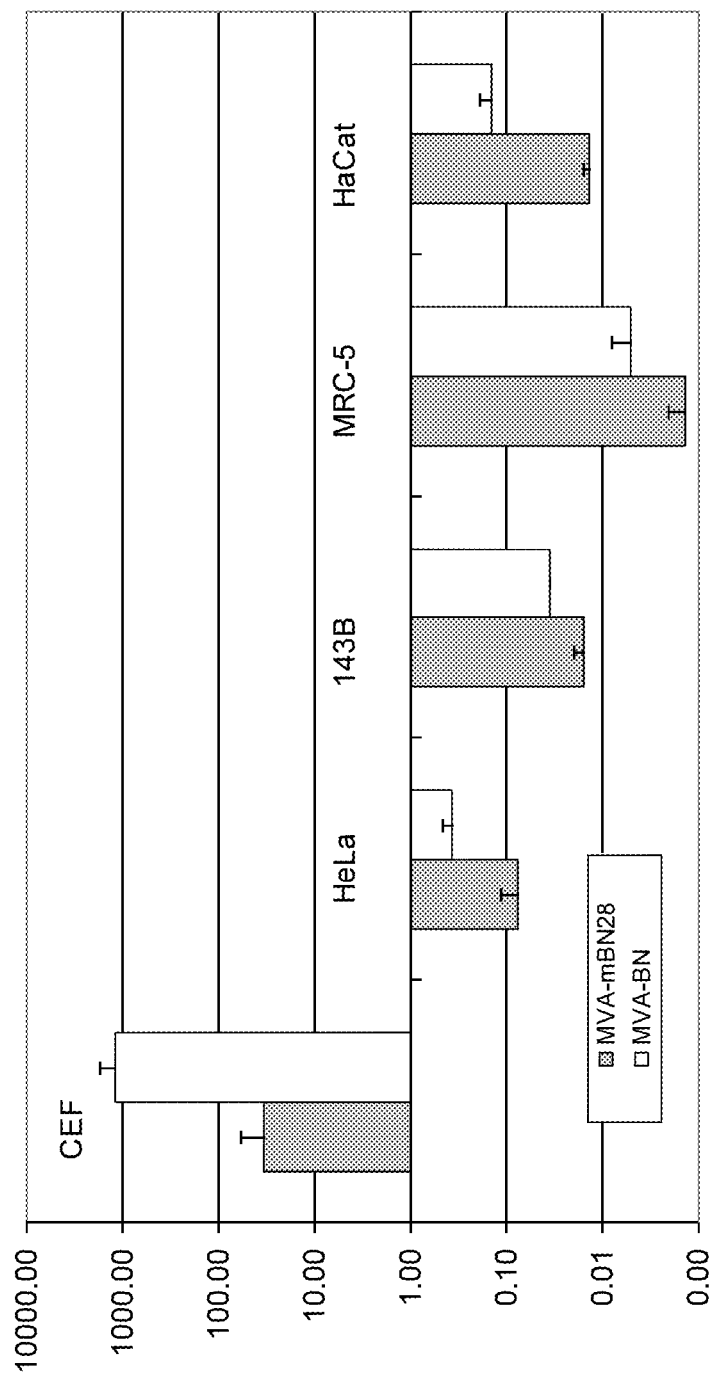

Resulting recombinant viruses were identified by standard PCR assays using a primer pair selectively amplifying the expected insertion site. To amplify the IGR07-08 insertion side primer pair, BN902 (ctggataaatacgaggacgtg, SEQ ID NO.: 16) and BN903 (gacaattatccgacgcaccg, SEQ ID NO.: 17) were used. In case the DNA of the empty vector virus MVA is amplified the expected PCR fragment is 190 nucleotides (nt) long, in case a recombinant MVA for PrM2 is amplified, which has incorporated Denguevirus PrM2, coding region at the IGR07-08 insertion site, the fragment is expected to be 950 bp. The PCR results in FIG. 9a) show clearly the stable insertion of PrM2 in the IGR07-08 insertion site after 20 rounds of virus amplification. The recombinant MVA still shows the same growth characteristics as MVA-BN. It replicates in chicken embryo fibroblasts (CEF cells) and grows attenuated in mammalian cells (FIG. 9*b*).

Insertion of HIV env in the IGR07-08 Insertion Site of MVA

In a first round, cells were infected with MVA according to the above-described protocol and were additionally transfected with insertion vector pBN56 (FIG. 3*e*) containing the NPT gene for selection and EGFP as reporter gene. Resulting recombinant viruses were purified by 6 rounds of plaque purification under G418 selection.

Resulting recombinant viruses were identified by standard PCR assays using a primer pair selectively amplifying the expected insertion site. To amplify the IR07-08 insertion side primer pair, BN902 (ctggataaatacgaggacgtg, SEQ ID NO.: 16) and BN903 (gacaattatccgacgcaccg, SEQ ID NO.: 17) were used. In case the DNA of the empty vector virus MVA is amplified the expected PCR fragment is 190 nucleotides (nt) long, in case a recombinant MVA for env is amplified, which has incorporated HIV env coding region at the IGR07-08 insertion site, the fragment is expected to be 2.6 kb. The PCR results in FIG. 10 show clearly the stable insertion of env in the IGR07-08 insertion site after 20 rounds of virus amplification.

EXAMPLE 4

Insertion Vector pBNX80, pBNX87 and pBN47

The MVA sequences adjacent the new insertion site (at genome position 37330) between the ORF 044L and 045L were isolated by standard PCR amplification of the sequence of interest using the following primers:

IGR44/45F1up (CGCGAGCTCATTTCTTAGCTAGAGTGATA; SEQ ID NO.: 18) and IGR44/45F1end (AGGCCGCGGAGTGAAAGCTAGAGAGGG;

SEQ ID NO.: 19) for isolating Flank 1;

IGR44/45F2up (CCGCTCGAGCGCGGATCCTAAACTGTATCGATTATT;

SEQ ID NO.: 20) and IGR44/45F2end (CAGGGCCCCTAAATGCGCTTCTCAAT; SEQ ID NO.: 21) for isolating Flank 2.

The PCR fragment comprising Flank 1 was treated with the restriction enzymes SacII and SacI and ligated to a SacII/SacI digested and dephosphorylated basic vector, such as pBluescript (Stratagene).

The resulting plasmid was XhoI/ApaI digested, dephosphorylated and ligated to the XhoI/ApaI digested PCR fragment comprising Flank 2.

Optionally, a repetitive sequence of Flank 2, which had been isolated by PCR using the primers IGR44/45F2up (CCGCTCGAGCGCGGATCCTAAACTGTATCGATTATT; SEQ ID NO.: 20) and IGR44/45F2mid (TTTCTGCAGCCTTCCTGGGTTTGTATTAACG; SEQ ID NO.: 22) and which became BamHI/PstI digested, was inserted into the BamHI/PstI site of the resulting vector.

Any reporter or therapeutical gene comprising cassette, having e.g. a poxviral promoter, a marker gene, a poly-A region and optionally an IRES element, a further gene, e.g. expressing a therapeutically active substance or gene product, can be blunt ended with T4 DNA Polymerase (Roche) after an restriction digest and inserted into a suitable cloning site of the plasmid vector. Considering a reporter gene cassette the PstI, EcoRI, EcoRV, HindIII, AvaI or XhoI restriction enzyme site between Flank 2 and the Flank-2-repetition is preferred as cloning site. For the construction of pENX87 (FIG. 4*b*) the NPT/EGFP selection cassette was inserted in pBNX80 (FIG. 4*a*). Considering an expression unit for a therapeutic gene, comprising a therapeutic gene and an operably linked promoter, this expression unite is inserted into the PacI site.

A restriction map of exemplary vector constructs according to this example are disclosed in FIG. 4*a*) and b) (pBNX80, pBNX87).

The vector can be used to generate a recombinant MVA—following the above-mentioned protocol—carrying an exogenous sequence in the intergenic region between two adjacent ORFs. For the construction of pBN47 (FIG. 4*c*) the PrM of Denguevirus serotype 3 was cloned into pBNX87 (FIG. 4*b*).

Insertion of PrM3 in the IGR44-45 Insertion Site of MVA

In a first round, cells were infected with MVA according to the above-described protocol and were additionally transfected with insertion vector pBN47 (FIG. 4*c*) containing the NPT gene for selection and EGFP as reporter gene. Resulting recombinant viruses were purified by 3 rounds of plaque purification under G418 selection.

Resulting recombinant viruses were identified by standard PCR assays using a primer pair selectively amplifying the expected insertion site. To amplify the IGR44-45 insertion side primer pair, BN904 (cgttagacaacacaccgacgatgg, SEQ ID NO.: 23) and BN905 (cggatgaaaaatttttggaag, SEQ ID NO.: 24) were used. In case the DNA of the empty vector virus MVA is amplified the expected PCR fragment is 185 nucleotides (nt) long, in case a recombinant MVA for PrM3 is amplified, which has incorporated Denguevirus PrM3 coding region at the IGR44-45 insertion site, the fragment is expected to be 850 bp. The PCR results in FIG. 11*a*) show clearly the stable insertion of PrM3 in the IGR44-45 insertion site after 19 rounds of virus amplification. The recombinant MVA still shows the same growth characteristics as MVA-BN. It replicates in chicken embryo fibroblasts (CEF cells) and grows attenuated in mammalian cells (FIG. 11*b*).

EXAMPLE 5

Insertion Vector pBNX90, pBNX92 and pBN54

The MVA sequences adjacent the new insertion site (at genome position 137496) between the ORF 148R and 149L were isolated by standard PCR amplification of the sequence of interest using the following primers:

IGR148/149F1up (TCCCCGCGGGGACTCATAGATTATCGACG;

SEQ ID NO.: 25) and IGR148/149F1end (CTAGTCTAGACTAGTCTATTAATCCACAGAAATAC; SEQ ID NO.: 26) for isolating Flank 1;

IGR148/149F2up (CCCAAGCTTGGGCGGGATCCCGTTTCTAGTATGGGGATC; SEQ ID NO.: 27) and

IGR148/149F2end (TAGGGCCCGTTATTGCCATGATA-GAG; SEQ ID NO.: 28) for isolating Flank 2.

The PCR fragment comprising Flank 1 was treated with the restriction enzymes SacII and XbaI and ligated to a SacII/XbaI digested and dephosphorylated basic vector, such as pBluescript (Stratagene).

The resulting plasmid was HindIII/ApaI digested, dephosphorylated and ligated to the HindIII/ApaI digested PCR fragment comprising Flank 2.

Optionally, a repetitive sequence of Flank 2, which had been isolated by PCR using the primers IGR148/149F2up (CCCAAGCTTGGGCGGGATC-CCGTTTCTAGTATGGGGATC; SEQ ID NO.: 27) and IGR148/149F2mid (TTTCTGCAGTGTATAATACCAC-GAGC; SEQ ID NO.: 29) and which became BamHI/PstI digested, was inserted into the BamHI/PstI site of the resulting vector.

Any reporter or therapeutical gene comprising cassette, having e.g. a poxviral promoter, a marker gene, a poly-A region and optionally an IRES element, a further gene, e.g. expressing a therapeutically active substance or gene product, can be blunt ended with T4 DNA Polymerase (Roche) after an restriction digest and inserted into a suitable cloning site of the plasmid vector. For construction of pBNX92 (FIG. 5b) the gpt/BFP expression cassette was inserted in this cloning site. Considering a reporter gene cassette the PstI, EcoRI, EcoRV and HindIII restriction enzyme site between Flank 2 and the Flank-2-repetition is preferred as cloning site. Considering an expression unit for a therapeutic gene, comprising a therapeutic gene and an operably linked promoter, this expression unite is inserted into the PacI site. For construction of pBN54 (FIG. 5c) the Denguevirus PrM1 was inserted in this PacI site.

Figure 5A:
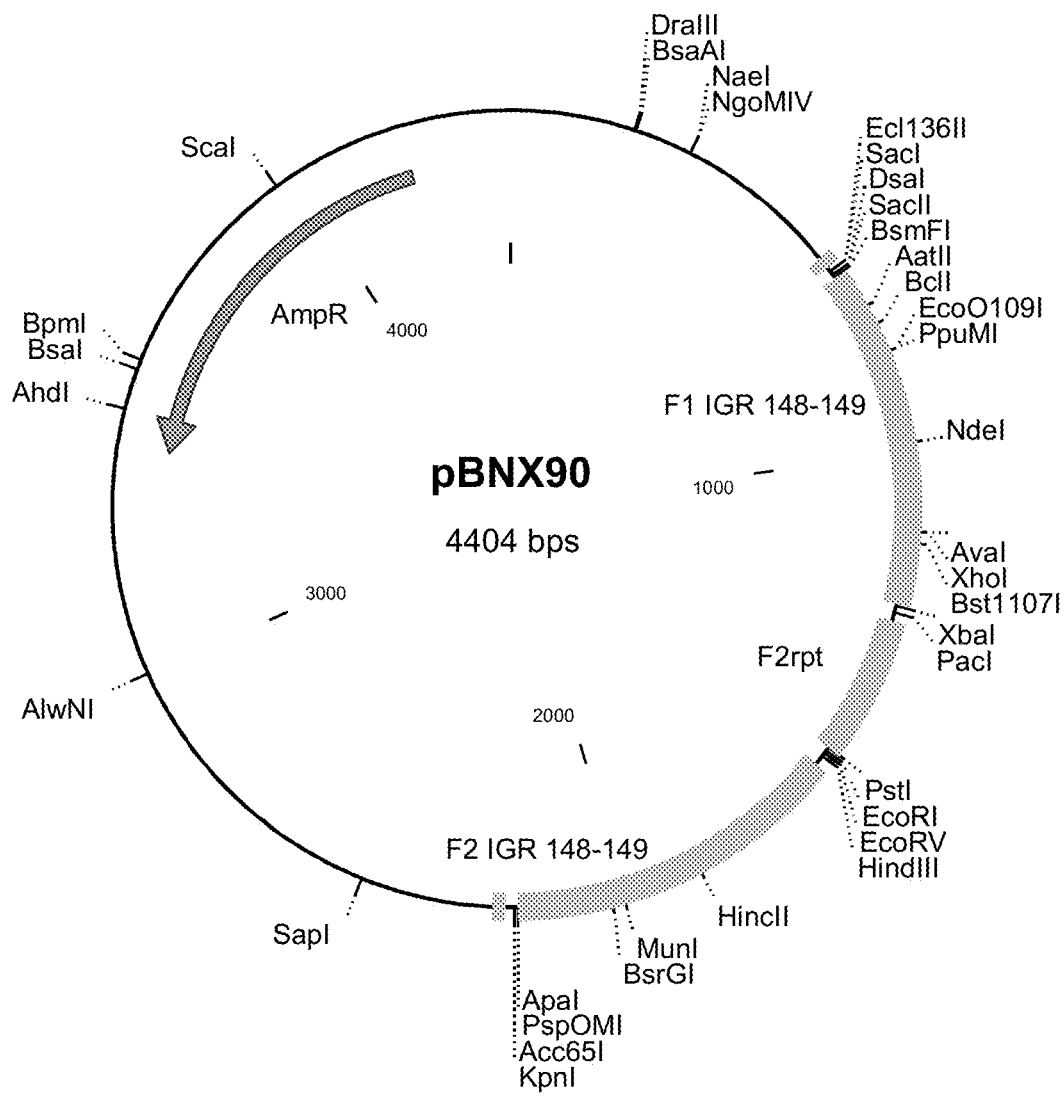
Figure 5B:
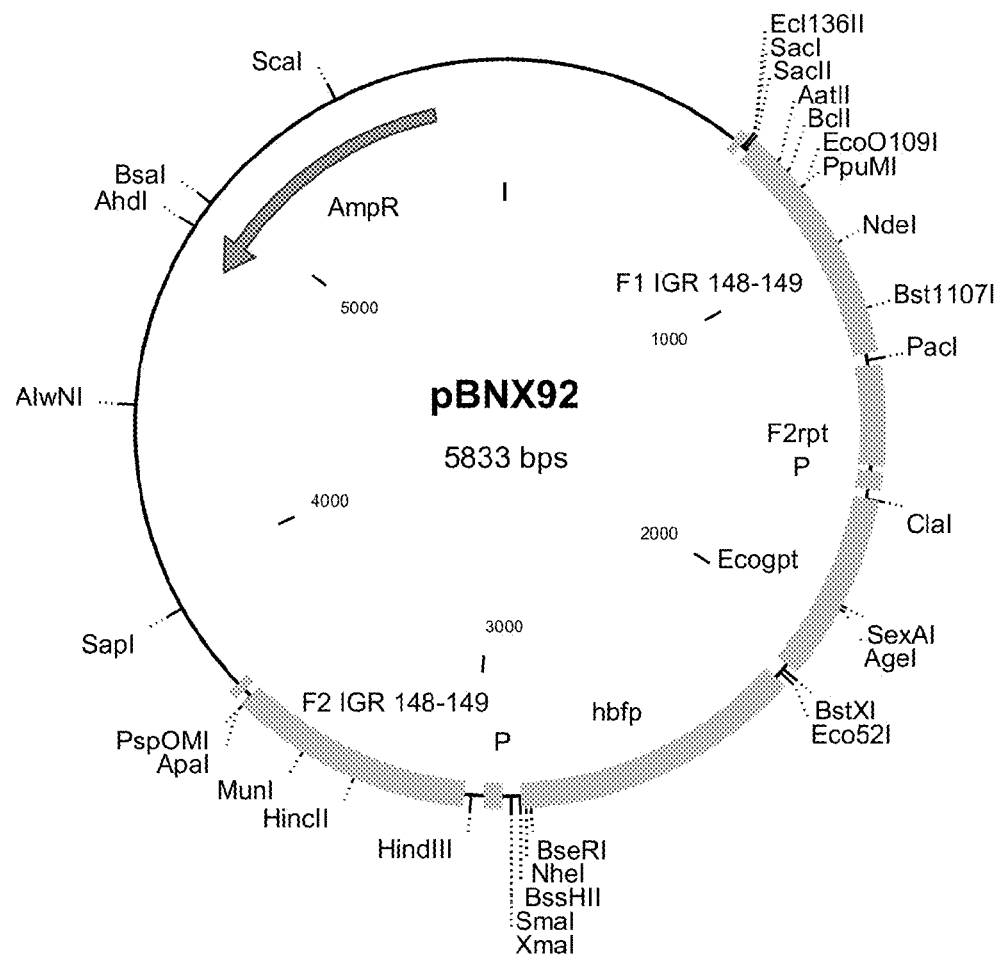
Figure 5C:
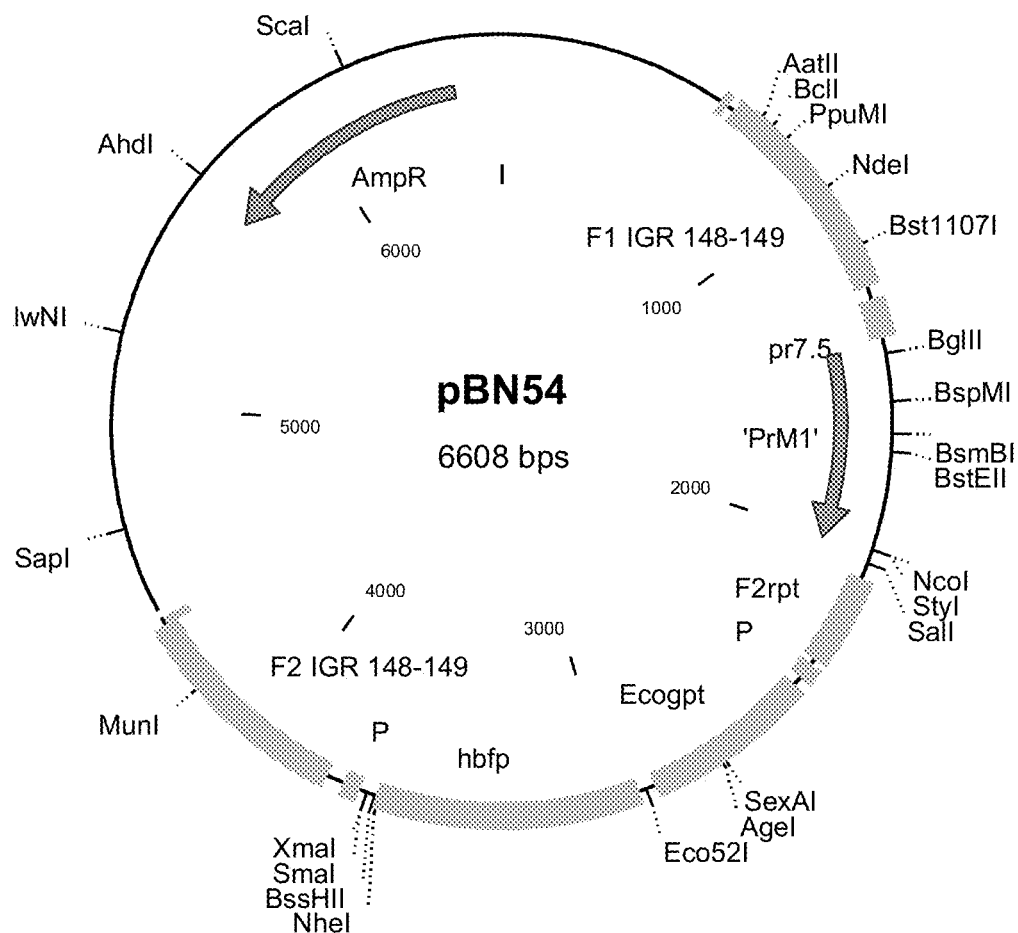
Figure 6:
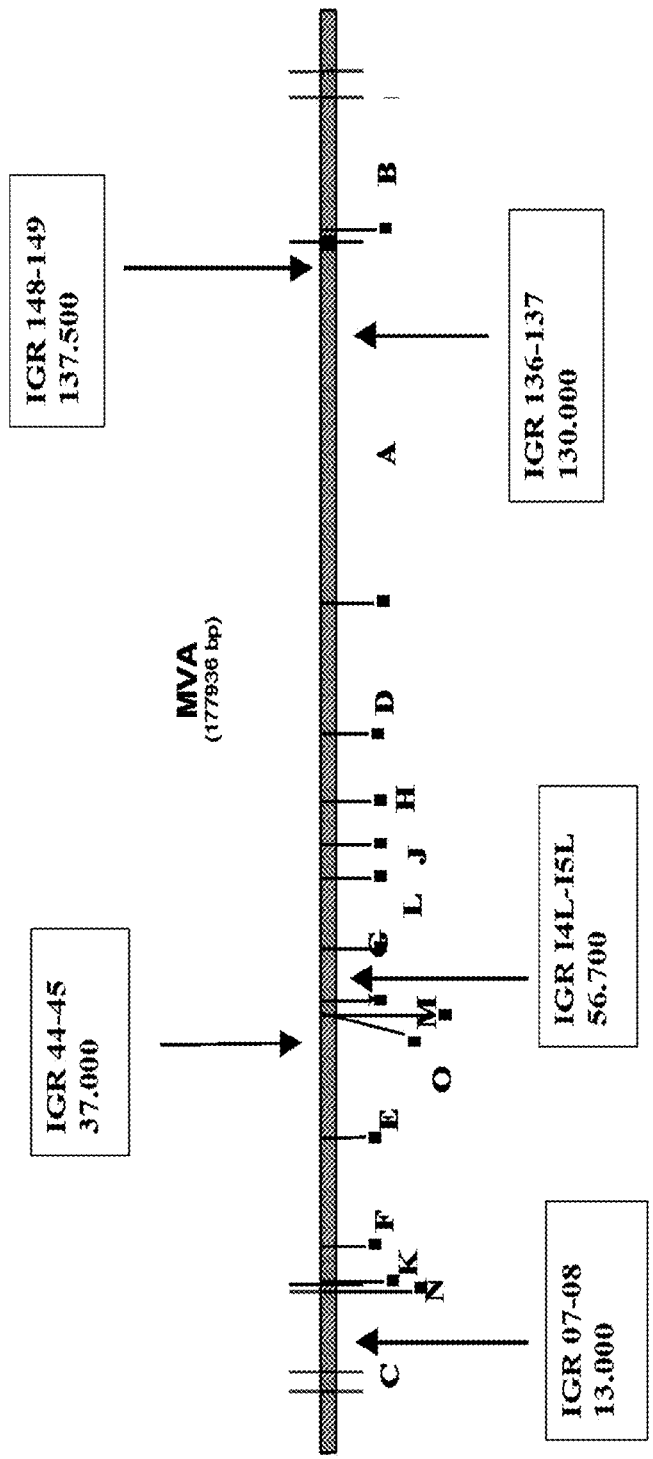

A restriction map of an exemplary vector construct according to this Example is disclosed in FIG. 5a) and b) (pBNX90, pBNX92).

The vector can be used to generate a recombinant MVA—following the above-mentioned protocol—carrying an exogenous sequence in the intergenic region between two adjacent ORFs. For the generation of a recombinant MVA expressing the Denguevirus PrM1 pEN54 (FIG. 5c) was used for a homologous recombination.

Insertion of PrM1 in the IGR148-149 Insertion Site of MVA

In a first round, cells were infected with MVA according to the above-described protocol and were additionally transfected with insertion vector pEN54 (FIG. 5c) containing the gpt gene for selection and BFP as reporter gene. Resulting recombinant viruses were purified by 3 rounds of plaque purification under selection with mycophenolic acid.

Figure 12A:
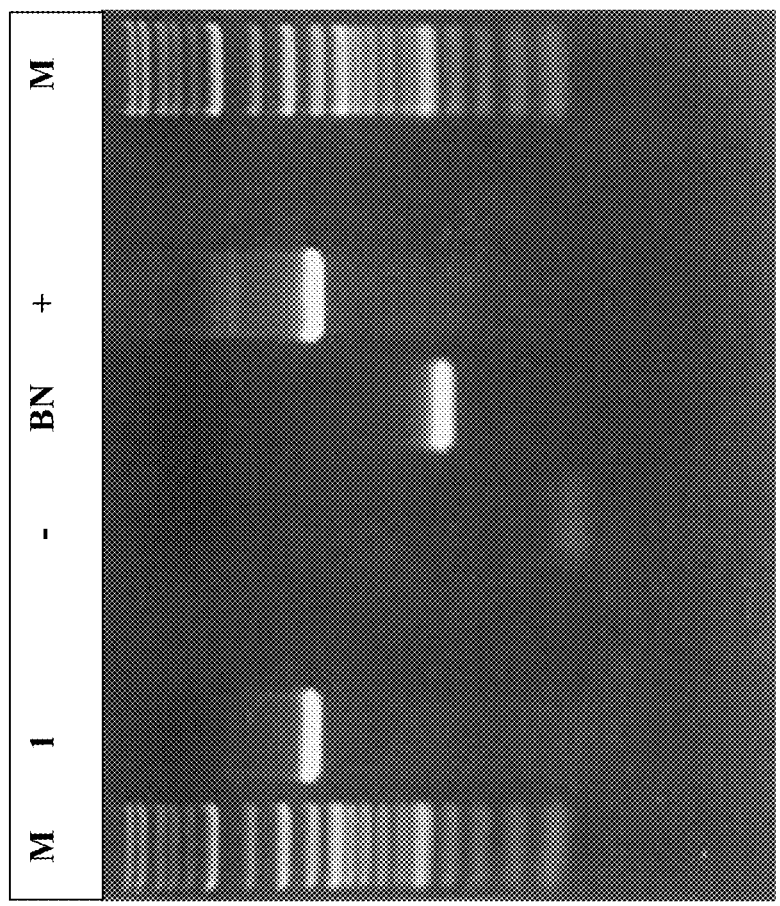
Figure 12B:
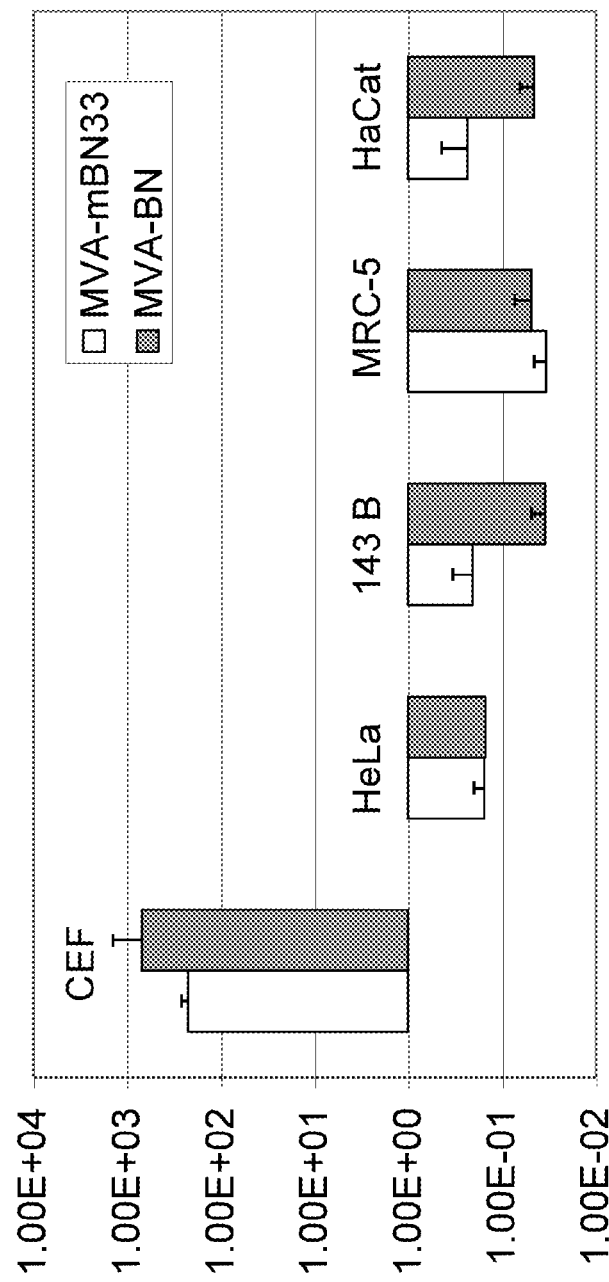

Resulting recombinant viruses were identified by standard PCR assays using a primer pair selectively amplifying the expected insertion site. To amplify the IGR148-149 insertion side primer pair, BN960 (ctgtataggtatgtcctctgcc, SEQ ID NO.: 30) and BN961 (gctagtagacgtggaaga, SEQ ID NO.: 31) were used. In case the DNA of the empty vector virus MVA is amplified the expected PCR fragment is 450 nucleotides (nt) long, in case a recombinant MVA for PrM1 is amplified, which has incorporated Denguevirus PrM1 coding region at the IGR148-149 insertion site, the fragment is expected to be 1200 bp. The PCR results in FIG. 12 a) show clearly the stable insertion of PrM1 in the IGR148-149 insertion site after 23 rounds of virus amplification. The recombinant MVA still shows the same growth characteristics as MVA-BN. It replicates in chicken embryo fibroblasts (CEF cells) and grows attenuated in mammalian cells (FIG. 12 b).

The invention claimed is:

1. A recombinant Modified Vaccinia Ankara (MVA) virus comprising a heterologous DNA sequence inserted into an intergenic region (IGR) of the viral genome, wherein the IGR is IGR 088R-089L.

2. The recombinant MVA virus of claim 1, wherein the heterologous DNA sequence comprises a coding sequence.

3. The recombinant MVA virus of claim 2, wherein the coding sequence is placed under the transcriptional control of a poxviral transcription control element.

4. The recombinant MVA virus of claim 2, wherein the coding sequence encodes at least one protein, polypeptide, peptide, foreign antigen, or antigenic epitope.

5. The recombinant MVA virus of claim 1, wherein the heterologous DNA sequence comprises a sequence from Dengue virus.

6. The recombinant MVA virus of claim 1, wherein the heterologous DNA sequence comprises a sequence from Japanese encephalitis virus.

7. The recombinant MVA virus of claim 1, wherein the heterologous DNA sequence comprises a sequence from Hepatitis virus B.

8. The recombinant MVA virus of claim 1, wherein the heterologous DNA sequence comprises a sequence from Hepatitis virus C.

9. The recombinant MVA virus of claim 1, wherein the heterologous DNA sequence comprises a sequence from human immunodeficiency virus (HIV).

10. The recombinant MVA virus of claim 5, wherein the Dengue virus sequence is selected from the group consisting of NS1 and PrM sequences.

11. An immunogenic composition comprising the recombinant MVA virus of claim 1 and a physiologically acceptable carrier, diluent, adjuvant, or additive.

12. The immunogenic composition of claim 11, wherein the heterologous DNA sequence comprises a sequence from Dengue virus, Japanese encephalitis virus, Hepatitis virus B, Hepatitis virus C, or human immunodeficiency virus (HIV).

13. An isolated cell comprising the recombinant MVA virus of claim 1.

14. A plasmid vector comprising a DNA sequence derived from or homologous to the genome of an MVA virus, wherein the DNA sequence comprises a complete IGR or a fragment of an IGR, wherein inserted into said IGR is a cloning site for the insertion of an exogenous DNA sequence, and wherein the IGR is IGR 088R-089L.

15. An isolated cell comprising the plasmid vector of claim 14.

16. A method for inducing an immune response in an animal comprising administering the recombinant modified vaccinia Ankara virus of claim 1 to an animal.

17. The method of claim 16, wherein the heterologous DNA sequence comprises a sequence from Dengue virus, Japanese encephalitis virus, Hepatitis virus B, Hepatitis virus C, or human immunodeficiency virus (HIV).

18. A method for introducing a heterologous DNA sequence into a cell comprising infecting the cell with the recombinant modified vaccinia Ankara virus of claim 1.

19. The method of claim 18, wherein the heterologous DNA sequence comprises a sequence from Dengue virus, Japanese encephalitis virus, Hepatitis virus B, Hepatitis virus C, or human immunodeficiency virus (HIV).

20. A method for producing a recombinant modified vaccinia Ankara virus comprising:
   (a) transfecting a cell with the plasmid vector of claim 14;
   (b) infecting the transfected cell with an MVA; and
   (c) isolating a recombinant MVA comprising the heterologous DNA.

\* \* \* \* \*

SEQUENCE LISTING

```
<160> NUMBER OF SEQ ID NOS: 37

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
caactctctt cttgattacc                                                     20

<210> SEQ ID NO 2
<211> LENGTH: 19
<212> TYPE: DNA
<213> ORGANISM: artificial
<220> FEATURE:
<223> OTHER INFORMATION: primer

<400> SEQUENCE: 2
cgatcaaagt caatctatg                                                      19

<210> SEQ ID NO 3
<211> LENGTH: 33
<212> TYPE: DNA
<213> ORGANISM: artificial
<220> FEATURE:
<223> OTHER INFORMATION: primer

<400> SEQUENCE: 3
tccccgcgga gaggcgtaaa agttaaatta gat                                      33
```

<210> SEQ ID NO 4
<211> LENGTH: 33
<212> TYPE: DNA
<213> ORGANISM: artificial
<220> FEATURE:
<223> OTHER INFORMATION: primer

<400> SEQUENCE: 4
tgatctagaa tcgctcgtaa aaactgcgga ggt                                   33

<210> SEQ ID NO 5
<211> LENGTH: 29
<212> TYPE: DNA
<213> ORGANISM: artificial
<220> FEATURE:
<223> OTHER INFORMATION: primer

<400> SEQUENCE: 5
ccgctcgagt tcacgttcag ccttcatgc                                       29

<210> SEQ ID NO 6
<211> LENGTH: 32
<212> TYPE: DNA
<213> ORGANISM: artificial
<220> FEATURE:
<223> OTHER INFORMATION: primer

<400> SEQUENCE: 6
cgggggccct attttgtata atatctggta ag                                   32

<210> SEQ ID NO 7
<211> LENGTH: 35
<212> TYPE: DNA
<213> ORGANISM: artificial
<220> FEATURE:
<223> OTHER INFORMATION: primer

<400> SEQUENCE: 7
cggctgcagg gtaccttcac gttcagcctt catgc                                35

<210> SEQ ID NO 8
<211> LENGTH: 34
<212> TYPE: DNA
<213> ORGANISM: artificial
<220> FEATURE:
<223> OTHER INFORMATION: primer

<400> SEQUENCE: 8
cggaagcttt atatggttta ggatattctg tttt                                 34

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
cgttcgcatg ggttacctcc                                                 20

<210> SEQ ID NO 10
<211> LENGTH: 18
<212> TYPE: DNA
<213> ORGANISM: artificial
<220> FEATURE:
<223> OTHER INFORMATION: primer -continued

<400> SEQUENCE: 10
gacgcatgaa ggctgaac                                                18

<210> SEQ ID NO 11
<211> LENGTH: 27
<212> TYPE: DNA
<213> ORGANISM: artificial
<220> FEATURE:
<223> OTHER INFORMATION: primer

<400> SEQUENCE: 11
cgcgagctca ataaaaaaaa gttttac                                      27

<210> SEQ ID NO 12
<211> LENGTH: 29
<212> TYPE: DNA
<213> ORGANISM: artificial
<220> FEATURE:
<223> OTHER INFORMATION: primer

<400> SEQUENCE: 12
aggccgcgga tgcatgttat gcaaaatat                                    29

<210> SEQ ID NO 13
<211> LENGTH: 36
<212> TYPE: DNA
<213> ORGANISM: artificial
<220> FEATURE:
<223> OTHER INFORMATION: primer

<400> SEQUENCE: 13
ccgctcgagc gcggatccca atatatggca tagaac                            36

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
cagggccctc tcatcgcttt catg                                         24

<210> SEQ ID NO 15
<211> LENGTH: 28
<212> TYPE: DNA
<213> ORGANISM: artificial
<220> FEATURE:
<223> OTHER INFORMATION: primer

<400> SEQUENCE: 15
tttctgcagt gatatttatc caatacta                                     28

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
ctggataaat acgaggacgt g                                            21

<210> SEQ ID NO 17
<211> LENGTH: 20

```
<212> TYPE: DNA
<213> ORGANISM: artificial
<220> FEATURE:
<223> OTHER INFORMATION: primer

<400> SEQUENCE: 17
gacaattatc cgacgcaccg                                            20

<210> SEQ ID NO 18
<211> LENGTH: 29
<212> TYPE: DNA
<213> ORGANISM: artificial
<220> FEATURE:
<223> OTHER INFORMATION: primer

<400> SEQUENCE: 18
cgcgagctca tttcttagct agagtgata                                  29

<210> SEQ ID NO 19
<211> LENGTH: 27
<212> TYPE: DNA
<213> ORGANISM: artificial
<220> FEATURE:
<223> OTHER INFORMATION: primer

<400> SEQUENCE: 19
aggccgcgga gtgaaagcta gagaggg                                    27

<210> SEQ ID NO 20
<211> LENGTH: 36
<212> TYPE: DNA
<213> ORGANISM: artificial
<220> FEATURE:
<223> OTHER INFORMATION: primer

<400> SEQUENCE: 20
ccgctcgagc gcggatccta aactgtatcg attatt                          36

<210> SEQ ID NO 21
<211> LENGTH: 26
<212> TYPE: DNA
<213> ORGANISM: artificial
<220> FEATURE:
<223> OTHER INFORMATION: primer

<400> SEQUENCE: 21
cagggcccct aaatgcgctt ctcaat                                     26

<210> SEQ ID NO 22
<211> LENGTH: 31
<212> TYPE: DNA
<213> ORGANISM: artificial
<220> FEATURE:
<223> OTHER INFORMATION: primer

<400> SEQUENCE: 22
tttctgcagc cttcctgggt tgtattaac g                                31

<210> SEQ ID NO 23
<211> LENGTH: 24
<212> TYPE: DNA
<213> ORGANISM: artificial
<220> FEATURE:
<223> OTHER INFORMATION: primer

<400> SEQUENCE: 23
cgttagacaa cacaccgacg atgg                                       24
```

<210> SEQ ID NO 24
<211> LENGTH: 21
<212> TYPE: DNA
<213> ORGANISM: artificial
<220> FEATURE:
<223> OTHER INFORMATION: primer

<400> SEQUENCE: 24
cggatgaaaa atttttggaa g                                           21

<210> SEQ ID NO 25
<211> LENGTH: 29
<212> TYPE: DNA
<213> ORGANISM: artificial
<220> FEATURE:
<223> OTHER INFORMATION: primer

<400> SEQUENCE: 25
tccccgcggg gactcataga ttatcgacg                                   29

<210> SEQ ID NO 26
<211> LENGTH: 35
<212> TYPE: DNA
<213> ORGANISM: artificial
<220> FEATURE:
<223> OTHER INFORMATION: primer

<400> SEQUENCE: 26
ctagtctaga ctagtctatt aatccacaga aatac                            35

<210> SEQ ID NO 27
<211> LENGTH: 39
<212> TYPE: DNA
<213> ORGANISM: artificial
<220> FEATURE:
<223> OTHER INFORMATION: primer

<400> SEQUENCE: 27
cccaagcttg ggcgggatcc cgtttctagt atggggatc                        39

<210> SEQ ID NO 28
<211> LENGTH: 26
<212> TYPE: DNA
<213> ORGANISM: artificial
<220> FEATURE:
<223> OTHER INFORMATION: primer

<400> SEQUENCE: 28
tagggcccgt tattgccatg atagag                                      26

<210> SEQ ID NO 29
<211> LENGTH: 26
<212> TYPE: DNA
<213> ORGANISM: artificial
<220> FEATURE:
<223> OTHER INFORMATION: primer

<400> SEQUENCE: 29
tttctgcagt gtataatacc acgagc                                      26

<210> SEQ ID NO 30
<211> LENGTH: 22
<212> TYPE: DNA
<213> ORGANISM: artificial
<220> FEATURE:
<223> OTHER INFORMATION: primer

```
<400> SEQUENCE: 30
ctgtataggt atgtcctctg cc                                              22

<210> SEQ ID NO 31
<211> LENGTH: 18
<212> TYPE: DNA
<213> ORGANISM: artificial
<220> FEATURE:
<223> OTHER INFORMATION: primer

<400> SEQUENCE: 31
gctagtagac gtggaaga                                                   18

<210> SEQ ID NO 32
<211> LENGTH: 1192
<212> TYPE: DNA
<213> ORGANISM: vaccinia virus
<220> FEATURE:
<221> NAME/KEY: Fragment of ORF C 64L
<222> LOCATION: (1)..(526)
<220> FEATURE:
<221> NAME/KEY: IGR 64-65
<222> LOCATION: (527)..(608)
<220> FEATURE:
<221> NAME/KEY: Fragment of ORF C 65L
<222> LOCATION: (609)..(1190)

<400> SEQUENCE: 32
caccttctat agatctgaga atggatgatt ctccagtcga aacatattct accatggatc       60
cgtttaattt gttgatgaag atggattcat ccttaaatgt tttctctgta atagtttcca      120
ccgaaagact atgcaaagaa tttggaatgc gttccttgtg cttaatgttt ccatagacgg      180
cttctagaag ttgatacaac ataggactag ccgcggtaac ttttattttt agaaagtatc      240
catcgcttct atcttgttta gatttatttt tataaagttt agtctctcct tccaacataa      300
taaaagtgga agtcatttga ctagataaac tatcagtaag ttttatagag atagacgaac      360
aattagcgta ttgagaagca tttagtgtaa cgtattcgat acattttgca ttagatttac      420
taatcgattt tgcatactct ataacacccg cacaagtctg tagagaatcg ctagatgcag      480
taggtcttgg tgaagtttca actctcttct tgattacctt actcatgatt aaacctaaat      540
aattgtactt tgtaatataa tgatatatat tttcactttta tctcatttga gaataaaaat     600
gtttttgttt aaccactgca tgatgtacag atttcggaat cgcaaccac cagtggtttt       660 attttatcct tgtccaatgt gaattgaatg ggagcggatg cgggtttcgt acgtagatag      720
tacattcccg ttttagacc gagactccat ccgtaaaaat gcatactcgt tagtttggaa       780
taactcggat ctgctatatg gatattcata gattgacttt gatcgatgaa ggctcccctg      840
tctgcagcca tttttatgat cgtcttttgt ggaatttccc aaatagtttt ataaactcgc      900
ttaatatctt ctggaaggtt tgtattctga atggatccac catctgccat aatcctattc      960
ttgatctcat cattccataa ttttctctcg gttaaaactc taaggagatg cggattaact     1020
acttgaaatt ctccagacaa tactctccga gtgtaaatat tactggtata cggttccacc     1080
gactcattat ttcccaaaat ttgagcagtt gatgcagtcg gcataggtgc caccaataaa     1140
ctatttctaa gaccgtatgt tctgatttta tcttttagag gttcccaatt cc             1192

<210> SEQ ID NO 33
<211> LENGTH: 1200
<212> TYPE: DNA
<213> ORGANISM: vaccinia virus
<220> FEATURE:
```

```
<221> NAME/KEY: Fragment of ORF 135R
<222> LOCATION: (1)..(96)
<220> FEATURE:
<221> NAME/KEY: ORF C 136L
<222> LOCATION: (101)..(298)
<220> FEATURE:
<221> NAME/KEY: IGR 136-137
<222> LOCATION: (299)..(883)
<220> FEATURE:
<221> NAME/KEY: Fragment of ORF C 137L
<222> LOCATION: (884)..(1198)

<400> SEQUENCE: 33
agaggcgtaa aagttaaatt agatttcgaa cgaaggcctc cttcgtttta taaaccatta      60
gataaagttg atctcaaacc gtcttttctg gtgtaatatt ctagtttggt agtagataca     120
tatcaatatc atcaaattcg agatccgaat tataaaatgg gcgtggattg ttaactatag     180
aatcggacgt ctgatattcg aaaatctgtg gagttttagg ttttggtgga ggtgtaactg     240
ctacttggga tactgaagtc tgatattcag aaagctgggg gatgttctgg ttcgacatcc     300
accgatggtg tcacatcact aatcggttcg gtaacgtctg tggacgatgg aggcaccact     360
tctacaggtt ctggttcttt atcctcagtc atcaacggag ctacttcaat gcgaggaaat     420
gtataatttg gtaatggttt ctcatgtgga tctgaagaag aggtaagata tctactagaa     480
agataccgat cacgttctag ttctcttttg tagaacttaa cttttttcttt ctccgcatct    540
agttgatatt ccaacctctt cacgttcgca tgggttacct ccgcagtttt tacgagcgat    600
ttcacgttca gccttcatgc gtcttatagc atgaattcgc ttatcgttat cgggtttagc    660
ttctgtcacc ttagcaattc ctttttttatt aaactctaca taatcatatc catttctatt    720
gtttgttcta atataaacga gtatagcatc attgctaaat ttttcaatag tatcgaaaac    780
agaatatcct aaaccatata atatatattc aggaacactc aaactaaatg tccaggattc    840
tcctaaatac gtaaacttta atagtgcgaa atcattcaaa aatctaccac ttatagatag    900
atagatagta cataaatgcg tatagtagtc tacctatctc tttattatga aaaccggcat    960
tacgatcata tatgtcgtga tatacctgtg atccgtttac gttaaaccat aaatacatgg   1020
gtgatcctat aaacatgaat ttatttctaa ttctcagagc tatagttaat tgaccgtgta   1080
atatttgctt acatgcatac ttgatacgat cattaataag attttttatca ttgctcgtta   1140
tttcagaatc gtatatataa ggagtaccat cgtgattctt accagatatt atacaaaata   1200

<210> SEQ ID NO 34
<211> LENGTH: 1200
<212> TYPE: DNA
<213> ORGANISM: vaccinia virus
<220> FEATURE:
<221> NAME/KEY: Fragment of ORF 07R
<222> LOCATION: (1)..(338)
<220> FEATURE:
<221> NAME/KEY: IGR 07-08
<222> LOCATION: (339)..(852)
<220> FEATURE:
<221> NAME/KEY: Fragment of ORF C 08L
<222> LOCATION: (853)..(1200)

<400> SEQUENCE: 34
aataaaaaaa agttttacta atttaaaatt atttacattt ttttcactgt ttagtcgcgg      60
atatggaatt cgatcctgcc aaaatcaata catcatctat agatcatgta acaatattac     120
aatacataga tgaaccaaat gatataagac taacagtatg cattatcaca aaaataaatc     180
cacatttggc taatcaattt cgggcttgga aaaaacgtat cgccggaagg gactatatga     240
ctaacttatc tagagataca ggaatacaac aatcaaaact tactgaaact gtcaaaaaaa     300
```

```
tagaaacata tatggtctat atatacacta caatttagtt attaattgga taaccgatgt      360
gattatcaat caatattaag aaggttggta aattggtaca tagctaataa tacctataca      420
cccaataata caacaaccat ttctgagttg gatatcatca aaatactgga taaatacgag      480
gacgtgtata gagtaagtaa agaaaaagaa tgtgaaattt gctatgaagt tgtttactca      540
aaacgataga tactttggtt tattggattc gtgtaatcat atattttgca taacatgcat      600
caatatatgg catagaacac gaagagaaac cggtgcgtcg gataattgtc ctatatgtcg      660
tacccgtttt agaaacataa caatgagcaa gttaactaat aaataaaaag tttaatttgt      720
tgacgacgta tgtcgttatt ttttctcgta taaaagatta atttgattct aatataatct      780
ttagtattgg ataaatatca attcaaatta attccattag attatatcat aaataaaaat      840
agtagcacgc actacttcag ccaaatattc ttttttgaaa cgccatctat cgtagtgagg      900
acacaagtga acctataatg agcaaattta ttagtatcgg ttacatgaag gactttacgt      960
agagtggtga ttccactatc tgtggtacga acggtttcat cttctttgat gccatcaccc     1020
agatgttcta taaacttggt atcctttgcc aaccaataca tatagctaaa ctcaggcata     1080
tgttccacac atcctgaaca atgaaattct ccagaagatg ttacaatgtc tagatttgga     1140
catttggttt caaccgcgtt aacatatgag tgaacacacc catacatgaa agcgatgaga     1200
```

<210> SEQ ID NO 35
<211> LENGTH: 1200
<212> TYPE: DNA
<213> ORGANISM: vaccinia virus
<220> FEATURE:
<221> NAME/KEY: Fragment of ORF C 44L
<222> LOCATION: (1)..(375)
<220> FEATURE:
<221> NAME/KEY: IGR 44-45
<222> LOCATION: (376)..(647)
<220> FEATURE:
<221> NAME/KEY: Fragment of ORF C 45L
<222> LOCATION: (648)..(1200)

<400> SEQUENCE: 35
atttcttagc tagagtgata atttcgttaa aacattcaaa tgttgttaaa tgatcggatc 60
taaaatccat attttctggt agtgtttcta ccagcctaca ttttgctccc gcaggtaccg 120
gtgcaaatgg ccacatttag ttaacataaa aacttataca tcctgttcta tcaacgattc 180
tagaatatca tcggctatat cgctaaaatt ttcatcaaag tcgacatcac aacctaactc 240
agtcaatata ttaagaagtt ccatgatgtc atcttcgtct atttctatat ccgtatccat 300
tgtagattgt tgaccgatta tcgagtttaa atcattacta atactcaatc cttcagaata 360
caatctgtgt ttcattgtaa atttataggc ggtgtattta agttggtaga ttttcaatta 420
tgtatcaata tagcaacagt agttcttgct cctccttgat tctagcatcc tcttcattat 480
tttcttctac gtacataaac atgtccaata cgttagacaa cacaccgacg atggcggccg 540
ccacagacac gaatatgact aaaccgatga ccatttaaaa acccctctct agctttcact 600
taaactgtat cgattattct tttagaacat gtataatata aaaacattat tctatttcga 660
atttaggctt ccaaaaattt ttcatccgta aaccgataat aatatatata gacttgttaa 720
tagtcggaat aaatagatta atgcttaaac tatcatcatc tccacgatta gagatacaat 780
atttacattt tttttgctgt ttcgaaactt tatcaataca cgttaataca aacccaggaa 840
ggagatattg aaactgaggc tgttgaaaat gaaacggtga atacaataat tcagataatg 900
taaaatcatg attccgtatt ctgatgatat tagaactgct aatggatgtc gatggtatgt 960

```
atctaggagt atctatttta acaaagcatc gatttgctaa tatacaatta tcattttgat    1020
taattgttat tttattcata ttcttaaaag gtttcatatt tatcaattct tctacattaa    1080
aaatttccat ttttaattta tgtagccccg caatactcct cattacgttt cattttttgt    1140
ctataatatc cattttgttc atctcggtac atagattatc caattgagaa gcgcatttag    1200
```

<210> SEQ ID NO 36
<211> LENGTH: 1200
<212> TYPE: DNA
<213> ORGANISM: vaccinia virus
<220> FEATURE:
<221> NAME/KEY: Fragment of ORF 148R
<222> LOCATION: (1)..(596)
<220> FEATURE:
<221> NAME/KEY: IGR 148-149
<222> LOCATION: (597)..(855)
<220> FEATURE:
<221> NAME/KEY: Fragment of ORF C 149L
<222> LOCATION: (856)..(1200)

<400> SEQUENCE: 36

```
ctcatagatt atcgacgatt atactctgta ttagttctgt cggaggatgt gttatctcta     60
tagataatga cgtcaatggc aaaaatattc taacctttcc cattgatcat gctgtaatca    120
tatccccact gagtaaatgt gtcgtagtta gcaagggtcc tacaaccata ttggttgtta    180
aagcggatat acctagcaaa cgattggtaa catcgtttac aaacgacata ctgtatgtaa    240
acaatctatc actgattaat tattcgccgt tgtctgtatt cattattaga cgagttaccg    300
actatttgga tagacacata tgcgatcaga tatttgcgaa taataagtgg tattccatta    360
taaccatcga caataagcag tttcctattc catcaaactg tataggtatg tcctctgcca    420
agtacataaa ttctagcatc gagcaagata ctttaataca tgtttgtaac ctcgagcatc    480
cattcgactt agtatacaaa aaaatgcagt cgtacaattc tgtacctatc aaggaacaaa    540
tattgtacgg tagaattgat aatataaata tgagcattag tatttctgtg gattaataga    600
tttctagtat ggggatcatt aatcatctct aatctctaaa tacctcataa aacgaaaaaa    660
aagctattat caaatactgt acggaatgga ttcattctct tctcttttta tgaaactctg    720
ttgtatatct actgataaaa ctggaagcaa aaaatctgat aaaaagaata agaataagat    780
caaggattat tataaaataa caatagttcc tggttcctct tccacgtcta ctagctcgtg    840
gtattataca catgcctagt aatagtctct ttgcgttgac ggaaagcaga ctagaaataa    900
caggctaaaa tgttcagaca ccataatagt tcccaaccca gataataaca gagtaccatc    960
aacacattcc tttaaactca atcccaaacc caaaaccgtt aaaatgtatc cggccaattg   1020
atagtagata tgaggtgta cagcgcatga tgatttacac agtaaccaaa atgaaaatac    1080
tttagtaatt ataagaaata tagatggtaa cgtcatcatc aacaatccaa taatatgccg   1140
gagagtaaac attgacggat aaaacaaaaa tgctccgcat aactctatca tggcaataac   1200
```

<210> SEQ ID NO 37
<211> LENGTH: 1200
<212> TYPE: DNA
<213> ORGANISM: vaccinia virus
<220> FEATURE:
<221> NAME/KEY: Fragment of ORF 018L
<222> LOCATION: (1)..(399)
<220> FEATURE:
<221> NAME/KEY: IGR 018L-019L
<222> LOCATION: (400)..(607)
<220> FEATURE:
<221> NAME/KEY: Fragment of ORF C 019L
<222> LOCATION: (608)..(1081)
<220> FEATURE:

```
<221> NAME/KEY: non-coding region
<222> LOCATION: (1082)..(1200)

<400> SEQUENCE: 37
ggatgagtag ttttcttctt taactttata cttttttacta atcatatttta gactgatgta    60 tgggtaatag tgtttaaaga gttcgttctc atcatcagaa taaatcaata tctctgtttt    120
tttgttatac agatgtatta cagcctcata tattacgtaa tagaacgtgt catctacctt    180
attaactttc accgcatagt tgtttgcaaa tacggttaat cctttgacct cgtcgatttc    240
cgaccaatct gggcgtataa tgaatctaaa ctttaatttc ttgtaatcat tcgaaataat    300
ttttagtttg catccgtagt tatcccctt atgtaactgt aaatttctca acgcgatatc    360
tccattaata atgatgtcga attcgtgctg tatacccata ctgaatggat gaacgaatac    420
cgacggcgtt aatagtaatt tacttttca tctttacata ttgggtacta gttttactat    480
cataagttta taaattccac aagctactat ggaataagcc aaccatctta gtataacaca    540
catgtcttaa agtttattaa ttaattacat gttgtttat atatcgctac gaatttaaac    600
agagaaatca gtttaggaaa aaaaaatatc tatctacatc atcacgtctc tgtattctac    660
gatagagtgc tactttaaga tgagacatat ccgtgtcatc aaaaatatac tccattaaaa    720
tgattattcc ggcagcgaac ttgatattgg atatatcaca acctttgtta atatctacga    780
caatagacag cagtcccatg gttccataaa cagtgagttt atctttcttt gaagagatat    840
tttgtagaga tcttataaaa ctgtcgaatg acatcgcatt tatatcttta gctaaatcgt    900
atatgttacc atcgtaatat ctaaccgcgt ctatcttaaa cgtttccatc gctttaaaga    960
cgtttccgat agatggtctc atttcatcag tcatactgag ccaacaaata taatcgtgta    1020
taacatcttt gatagaatca gactctaaag aaaacgaatc ggctttatta tacgcattca    1080
tgataaactt aatgaaaaat gttttttcgtt gtttaagttg gatgaatagt atgtcttaat    1140
aattgttatt atttcattaa ttaatattta gtaacgagta cactctataa aaacgagaat    1200
```